United States Patent
Shturman et al.

(10) Patent No.: US 6,217,595 B1
(45) Date of Patent: *Apr. 17, 2001

(54) ROTATIONAL ATHERECTOMY DEVICE

(75) Inventors: Leonid Shturman, Minnetonka, MN (US); Andrei Nevzorov, Moscow (RU)

(73) Assignee: Shturman Cardiology Systems, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/225,370

(22) Filed: Jan. 4, 1999

Related U.S. Application Data

(62) Division of application No. 08/751,642, filed on Nov. 18, 1996, now abandoned.

(51) Int. Cl.[7] .................................................. A61B 17/00
(52) U.S. Cl. ........................................... 606/159; 242/430
(58) Field of Search ..................................... 606/159, 170, 606/171; 242/430; 83/907

(56) References Cited

U.S. PATENT DOCUMENTS

| | | |
|---|---|---|
| 1,481,078 | 1/1924 | Albertson . |
| 1,636,038 | 7/1927 | Bolozky et al. . |
| 1,785,345 | 12/1930 | Hasemann . |
| 2,570,335 | 10/1951 | Fitch . |
| 2,761,297 | 9/1956 | Buchsteiner . |
| 2,821,092 | 1/1958 | Cordora et al. . |
| 3,180,625 | 4/1965 | Wyzenbeek . |
| 3,937,222 | 2/1976 | Banko . |
| 4,112,708 | 9/1978 | Fukuda . |
| 4,424,045 | 1/1984 | Kulischenko et al. . |
| 4,445,509 | 5/1984 | Auth . |
| 4,607,626 | 8/1986 | Borodulin et al. . |
| 4,646,736 | 3/1987 | Auth . |
| 4,664,112 | 5/1987 | Kensey et al. . |
| 4,686,982 | 8/1987 | Nash . |
| 4,700,706 | 10/1987 | Kensey et al. . |
| 4,704,121 | 11/1987 | Moise . |
| 4,811,735 | 3/1989 | Nash et al. . |
| 4,976,689 | 12/1990 | Buchbinder et al. . |
| 4,990,134 | 2/1991 | Auth . |
| 5,158,564 | 10/1992 | Schnepp-Pesch et al. . |
| 5,192,291 | 3/1993 | Pannek, Jr. . |
| 5,217,474 | 6/1993 | Zacca et al. . |
| 5,246,420 | 9/1993 | Kraus et al. . |
| 5,273,052 | 12/1993 | Kraus et al. . |

(List continued on next page.)

FOREIGN PATENT DOCUMENTS

| | | |
|---|---|---|
| 1293663 | 11/1987 | (CA) . |
| 0 191 630 | 2/1986 | (EP) . |
| 0 268 228 | 11/1987 | (EP) . |
| 2055991 | 3/1996 | (RU) . |
| WO 97/09924 | 3/1997 | (WO) . |
| WO 98/02101 | 1/1998 | (WO) . |

*Primary Examiner*—Michael Buiz
*Assistant Examiner*—William Lewis
(74) *Attorney, Agent, or Firm*—Perman & Green, LLP

(57) ABSTRACT

A method of forming an elongate, flexible drive shaft which has utility as a rotational atherectomy device. In accordance with this method, an inner helical coil having a lumen and a proximal end is formed by winding a plurality of wires about a forming mandrel. An outer helical coil having a lumen and a proximal end is formed by winding a single wire with a mandrel-less coil forming machine. The inner helical coil is positioned within the outer helical coil to define a drive shaft. The inner and outer helical coils are oriented such that the inner helical coil is wound in a direction opposite that in which the outer helical coil is wound.

26 Claims, 16 Drawing Sheets

U.S. PATENT DOCUMENTS

| | | |
|---|---|---|
| 5,308,354 | 5/1994 | Zacca et al. . |
| 5,312,427 | 5/1994 | Shturman . |
| 5,314,407 | 5/1994 | Auth et al. . |
| 5,314,438 | 5/1994 | Shturman . |
| 5,318,576 * | 6/1994 | Plassche, Jr. et al. ............... 606/159 |
| 5,356,418 | 10/1994 | Shturman . |
| 5,358,485 | 10/1994 | Vance et al. . |
| 5,360,432 | 11/1994 | Shturman . |
| 5,395,311 | 3/1995 | Andrews . |
| 5,490,859 | 2/1996 | Mische et al. . |
| 5,501,694 | 3/1996 | Reeseman et al. . |
| 5,584,843 | 12/1996 | Wulfman et al. . |
| 5,766,190 * | 6/1998 | Wulfman ............................. 606/159 |

\* cited by examiner

ROTATIONAL ATHERECTOMY DEVICE

This application is a division of Ser. No. 08/751,642 filed Nov. 18, 1996, now abandoned.

FIELD OF THE INVENTION

The present invention provides an improved drive shaft for use with rotational atherectomy devices.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by a build-up of fatty deposits (atheromas) in the intimal layer (under the endothelium) of a patient's blood vessels. Very often over time, what Is initially deposited as relatively soft cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (issued to Auth), a rotating burr covered with an abrasive cutting material such as diamond grit (diamond particles or dust) is carried at the distal end of a flexible drive shaft. One atherectomy device commercially available from Heart Technologies, Inc. of Bellevue, Washington, U.S.A. is sold under the trade name Rotablator. The design of the Rotablator device is, to a significant extent, based on the design described in the Auth patent and the Rotablator device is typically rotated at speeds in the range of about 150,000–190,000 rpm.

Auth's burr is made from a solid, inflexible metal which is physically attached to a flexible, trifilar, helically wound drive shaft. This solid burr must be kept relatively short in order to allow the burr to navigate the bends and curves in tortuous arteries. At the same time, it must be sufficiently long to ensure reliable fixation of the burr to the drive shaft.

Another type of atherectomy device is shown in U.S. Pat. No. 5,314,438 (issued to Shturman). This design provides a solution for the problems associated with fixation of a separate burr to a drive shaft by eliminating the burr altogether. The abrasive drive shaft atherectomy device disclosed in the above-mentioned Shturman patent typically is used over a guide wire and includes a flexible, elongated drive shaft made from one or more helically wound wires. Wire turns of the proximal segment of the drive shaft have a generally constant diameter, while wire turns of a segment of the drive shaft near its distal end have an enlarged diameter. At least part of the enlarged diameter segment includes an external coating of an abrasive material to define an abrasive segment of the drive shaft which, when rotated at high speeds, is usable to remove stenotic tissue from an artery.

Manufacturing some of the embodiments of the device shown in the above-mentioned Shturman patent can be relatively time-consuming. This is particularly true with respect to the embodiments of the device which use two helically wound layers, such as the one shown in FIG. 8 of that reference. In that drawing and some of the other embodiments depicted in the Shturman patent, wire turns of the enlarged diameter segment of the drive shaft are supported by a bushing. Even though this bushing may be made of a flexible material, it does decrease somewhat the flexibility of the enlarged diameter abrasive segment of the drive shaft. Unless a bushing within the enlarged diameter segment is used, though, adjacent wire turns of this segment can fall out of alignment with one another when the enlarged diameter segment of the drive shaft is bent around a curve.

SUMMARY OF THE INVENTION

The present invention provides a novel rotational atherectomy device which includes an improved drive shaft and a method of making the same. Certain embodiments of the invention provide improvements over the atherectomy device taught in the Shturman patent mentioned above.

In accordance with a first embodiment, a rotational atherectomy device of the invention includes a flexible, elongated drive shaft having a central lumen for receipt of a guide wire therein around which the drive shaft may be rotated. The drive shaft has inner and outer co-axial wire layers helically wound in opposite directions so that the outer layer tends to radially contract and the inner layer tends to radially expand when the drive shaft is rotated in a predetermined direction. The outer layer of this embodiment comprises a mono-filar helically wound coil and the inner layer comprises a multi-filar helically wound coil received in the lumen of the outer layer. As explained below, this construction makes it easier to cost-effectively manufacture an appropriately shaped device with suitable mechanical properties. This drive shaft has proximal, intermediate and distal segments, with the outer layer of the intermediate segment of the drive shaft having a diameter which gradually increases distally through its proximal portion and gradually decreases distally through its distal portion, thereby defining an enlarged diameter segment of the drive shaft. At least part of this enlarged diameter segment desirably includes an external coating of an abrasive material to define an abrasive segment of the drive shaft which functions as an enlarged diameter tissue removal segment of the device. If wire turns along the distal portion of the intermediate segment are spaced from one another, then the abrasive material is optimally bonded to individual wire turns along at least part of the distal portion of the intermediate segment. If the wire turns of the outer layer along the abrasive segment are not spaced from one another, one can apply abrasive material using a binder which not only bonds abrasive material to the wire turns, but also bonds at least some of the wire turns to one another along at least part of the abrasive segment.

In keeping with a further embodiment of the invention, a rotational atherectomy device includes at least two helically wound wires forming inner and outer co-axial wire layers which preferably are helically wound in opposite directions, as mentioned above. The outer layer has an increased diameter along at least part of its length to define an enlarged diameter segment of the drive shaft. The precise shape of this enlarged diameter segment of the drive shaft can be varied. In accordance with this embodiment, wire turns of the inner layer of the drive shaft are spaced from one another along the enlarged diameter segment of the drive shaft. This has been found to further improve flexibility of the device while maintaining an appropriate shape in the enlarged diameter segment when the drive shaft is bent in operation, e.g. to keep wire turns of the enlarged diameter segment from falling out of alignment with one another when the drive shaft is bent or flexed to track curvatures of an artery or other vascular structure.

One preferred rotational atherectomy device of the invention includes a flexible, elongated drive shaft having at least two helically wound wires forming inner and outer co-axial wire layers helically wound in opposite directions so that the outer layer tends to radially contract and the inner layer tends to radially expand when the drive shaft is rotated in a predetermined direction. The drive shaft has proximal, intermediate and distal segments, with wire turns of the outer layer of the intermediate segment of the drive shaft having diameters that increase distally at a generally constant rate through a proximal portion of such intermediate segment thereby forming generally the shape of a cone. At least some adjacent wire turns of the inner layer of the intermediate segment of the drive shaft are spaced from one another, improving flexibility of the intermediate segment of the drive shaft. At least part of a distal portion of the intermediate segment of the outer layer includes an external coating of an abrasive material to define an abrasive segment of the drive shaft.

In another embodiment of the invention, an abrasive drive shaft atherectomy device includes a flexible, elongated drive shaft comprising at least one helically wound wire and having a central lumen for receipt of a guide wire therein around which the drive shaft may be rotated. As in the previous embodiment, this atherectomy device has proximal, intermediate and distal segments. The intermediate segment of the drive shaft has a diameter which gradually increases distally through its proximal portion and gradually decreases distally through its distal portion, thereby defining an enlarged diameter segment of the drive shaft. In addition, adjacent turns of the helically wound wire are spaced from one another along at least a portion of the enlarged diameter Intermediate segment, the spacing between adjacent wire turns along the intermediate segment gradually increasing distally through its proximal portion. In a preferred construction of this embodiment, the spacing between adjacent wire turns gradually decreases distally through the distal portion of the intermediate segment. At least part of the enlarged diameter intermediate segment includes an external coating of an abrasive material to define an abrasive segment of the drive shaft. If wire turns along the distal portion of the intermediate segment are spaced from one another, then the abrasive material is optimally bonded to individual wire turns along at least part of the distal portion of the intermediate segment. If the wire turns along the distal portion of the intermediate segment are not spaced from one another, one can apply abrasive material using a binder which not only bonds abrasive material to the wire turns, but also bonds at least some of the wire turns to one another along at least part of the distal portion of the intermediate segment.

It has been found that the wire turns of such an enlarged diameter intermediate segment have a reduced tendency to fall out of alignment with one another when the intermediate segment is being bent or flexed to track the curvatures of an artery or other vascular structure. Thus, it becomes possible to manufacture a sufficiently flexible enlarged diameter intermediate segment of the drive shaft with wire turns not supported by a bushing yet not falling out of alignment with each other, even when the Intermediate segment is bent.

Another aspect of the invention provides a method of manufacturing a flexible drive shaft for driving an operational element of a medical device. In accordance with one embodiment of this method, one forms an inner helical coil by winding a plurality of wires about a forming mandrel, yielding a coil having a lumen and a proximal end. An outer helical coil is formed by winding a single wire with a mandrel-less coil forming machine, also yielding a coil having a lumen and a proximal end. The inner helical coil is then positioned within the lumen of the outer helical coil, orienting the coils such that the inner helical coil is wound in a clockwise direction and the outer helical coil is wound in a counter-clockwise direction. (Depending on the direction in which the drive shaft is to be rotated, these relative orientations can be switched when viewed from the proximal end of the device, but they will, of course, have the opposite relative orientations when viewed from the distal end.) The proximal ends of the inner and outer helical coils may then be attached to a common driver and rotated.

One embodiment of this method is particularly well suited for producing rotational atherectomy devices. An inner helical coil is formed by winding a plurality of wires about a forming mandrel to yield a coil having a lumen, an intermediate segment and a proximal end, at least some adjacent wire turns being spaced from one another along at least part of the intermediate segment. An outer helical coil is formed by winding a single wire with a mandrel-less coil forming machine to produce a coil having a lumen, an intermediate segment and a proximal end, the diameters of the wire turns being gradually increased distally through a proximal portion of the intermediate segment and gradually decreased distally through a distal portion of the intermediate segment, thereby defining an enlarged diameter segment of the outer layer. The inner helical coil is positioned within the lumen of the outer helical coil, with the intermediate segment of the inner helical coil being positioned generally within the intermediate segment of the outer helical coil. The inner and outer helical coils are optimally oriented such that the inner helical coil is wound in a clockwise direction and the outer helical coil is wound in a counterclockwise direction. A length of the enlarged diameter segment of the outer helical coil is coated with an abrasive material to define an abrasive segment of the drive shaft. The abrasive material can be applied either before or after the inner layer is positioned within the outer layer.

DETAILED DESCRIPTION OF THE INVENTION

Figure 1:
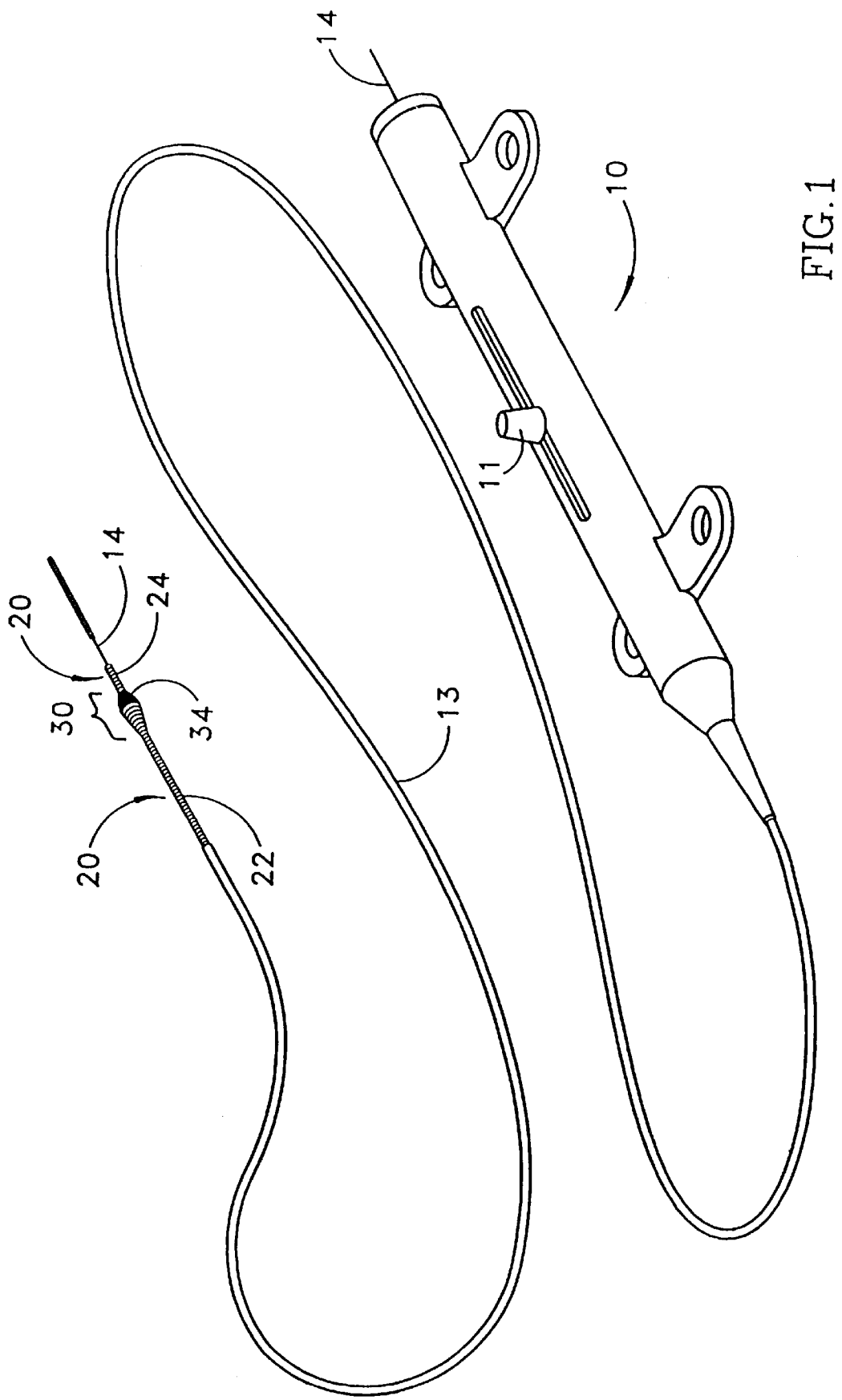
FIG. 1 is a perspective view of an atherectomy device of an embodiment of the invention.

FIG. 1 illustrates a typical rotational atherectomy device in accordance with at least some of the embodiments of the present invention. The device includes a handle portion 10, with an elongated, flexible drive shaft 20 and an elongated catheter 13 extending distally from the handle portion 10. The drive shaft 20 includes a proximal segment 22, an enlarged diameter intermediate segment 30 and a distal segment 24. At least part of the distal portion 34 of the enlarged diameter intermediate segment 30 is coated with an abrasive material and defines an enlarged diameter tissue removal segment of the drive shaft. The catheter 13 has a lumen in which most of the proximal segment of the drive shaft 20 is disposed. The balance of the proximal segment 22, the enlarged diameter intermediate segment and the distal segment 24 extend distally beyond the distal end of the catheter 13. The drive shaft 20 also includes an inner lumen, permitting the drive shaft 20 to be advanced and rotated over a guide wire 14.

The handle 10 desirably contains a driver, such as a turbine or similar rotational drive mechanism, for rotating the drive shaft 20. The handle 10 typically may be connected to a power source (such as compressed gas) and a source of physiological solution (used for cooling and lubrication) delivered through suitable tubing, neither of which are illustrated for the sake of clarity. The handle 10 also desirably includes a control knob 11 for advancing and retracting the driver and drive shaft 20 with respect to the catheter 13 and the body of the handle. Details regarding such handles and associated instrumentation are well known in the industry, and are described, e.g., in U.S. Pat. No. 5,314,407 (issued to Auth) and U.S. Pat. No. 5,314,438 (issued to Shturman), the teachings of which are incorporated herein by reference. The details of the handle form no part of this invention and need not be described in any great detail here.

Figure 2:
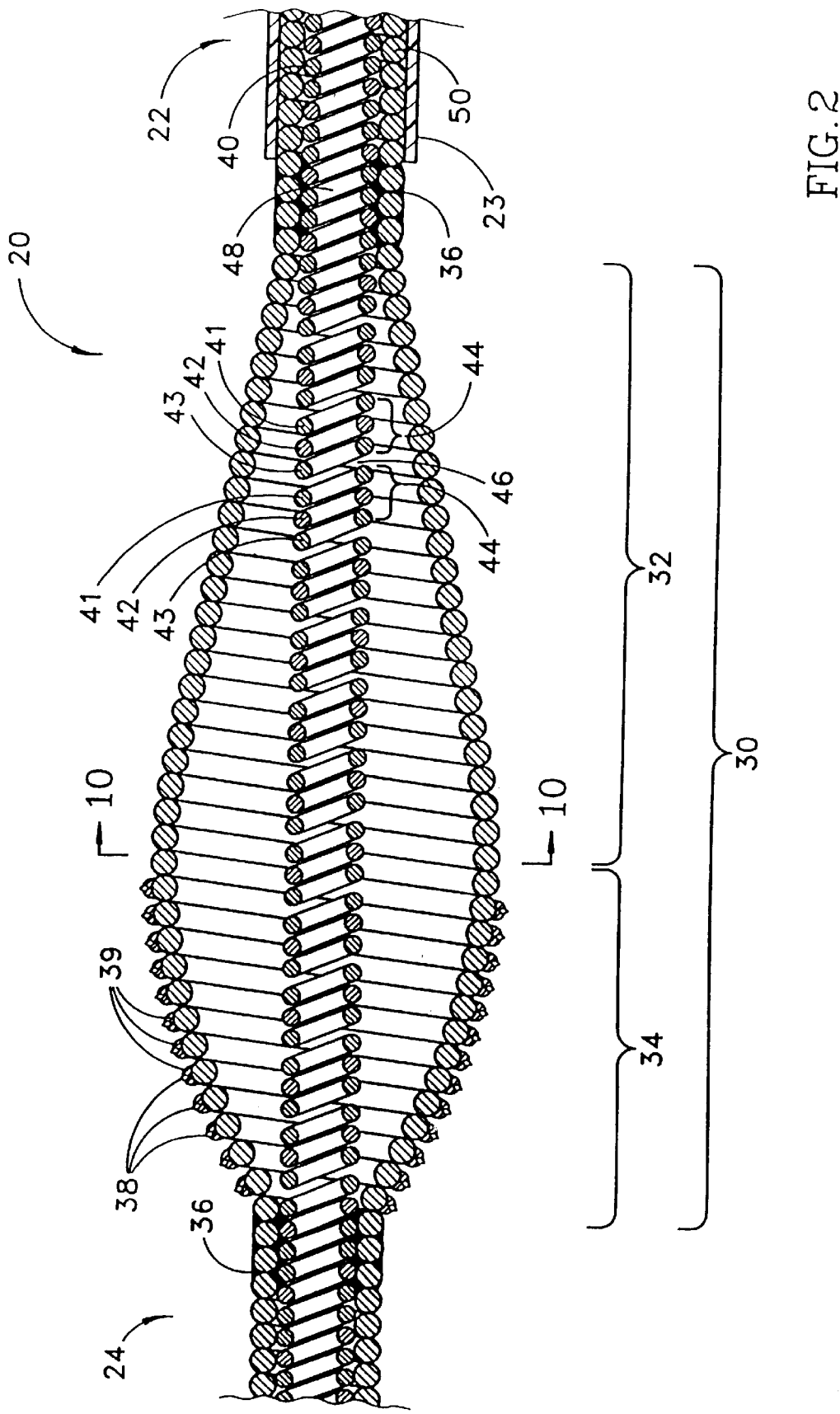
FIG. 2 is a broken-away, longitudinal cross-sectional view of the enlarged diameter segment of the drive shaft of the atherectomy device shown in FIG. 1.

FIGS. 2–7 and 10–16 all illustrate different embodiments of medical devices incorporating a flexible, elongated drive shaft in accordance with the present invention. Turning first to FIG. 2, this drive shaft generally includes an inner helical layer 40 and an outer helical layer 50. Each of these layers comprises a wire or wires helically wound to define a helical coil. These two helical layers of the drive shaft are desirably arranged such that the inner helical layer 40 is received within the lumen of the outer helical layer 50 in a generally co-axial fashion.

The inner and outer helical layers optimally are helically wound in opposite directions and have their proximal ends attached to a common driver, such as the turbine noted above. When the driver is actuated in a predetermined rotational direction, this will apply torque to the proximal end of the drive shaft 20 and the outer helical layer 50 will tend to radially contract while the inner helical layer 40 will tend to radially expand, urging the two wire layers into radially compressive engagement. These two wire layers thus support one another and prevent the outer diameter of the drive shaft from significantly increasing or the diameter of the lumen 48 of the inner layer from appreciably decreasing. This permits the drive shaft to be used within a catheter of a fixed size and rotated about a guide wire without having to worry about the drive shaft locking up against the lumen of the catheter or locking down on the guide wire.

Such a structure is generally disclosed in Shturman's U.S. Pat. No. 5,314,438, the teachings of which have been incorporated herein by reference. For example, FIGS. 7, 8 and 22 of that Shturman patent show an atherectomy device using a drive shaft with a two-layer construction. It has been found, though, that such a construction can be relatively difficult and time-consuming to manufacture, particularly where the two-layer construction is used along the entire length of the drive shaft of the type shown in FIG. 8 of the Shturman patent.

In accordance with one embodiment of the present invention, the inner helical layer 40 comprises a plurality of wires (i.e., is multi-filar) while the outer helical layer Is formed of a single wire (i.e., is mono-filar). This provides a number of substantial advantages over the prior art design reflected in the above-mentioned Shturman patent. For example, a drive shaft 20 in accordance with the present invention is believed to yield superior torque-delivering capabilities over a device which uses mono-filar inner and outer layers (provided that all of the wires employed in the inner helical layer 40 each have the same diameter as the single wire in a mono-filar inner layer). As discussed in more detail below, the drive shaft of the present invention can be manufactured fairly cost effectively without compromising tolerance requirements of the lumen 48 of the drive shaft or unduly limiting the ability to modify the exterior shape of the enlarged diameter segment of the outer layer 50 to meet varied design objectives.

In a particularly preferred embodiment, the inner helical layer 40 is comprised of at least three wires, illustrated in FIG. 2 as first, second and third wires 41, 42 and 43, respectively. This plurality of wires can be wound about a forming mandrel using techniques well known in the medical device industry. Each of the wires 41, 42 and 43 can be arranged immediately adjacent one another to yield a coil wherein adjacent turns are formed from different wires. Groups 44 of these three wires can be positioned essentially without gaps (as shown in the proximal segment 22) or with gaps 46 between adjacent turns of groups of wires to enhance flexibility.

Figure 10:
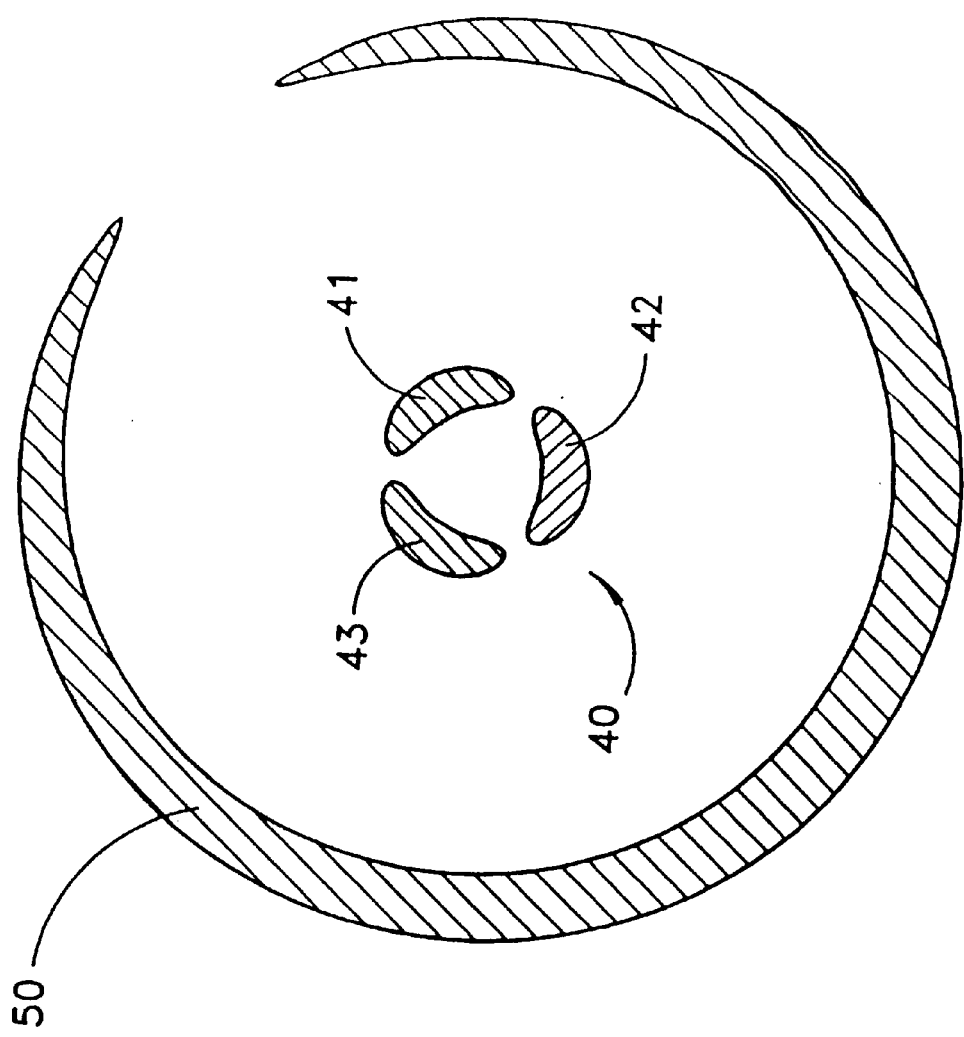
FIG. 10 is a schematic cross-sectional view of the drive shaft of the atherectomy device of FIG. 2 taken along lines 10—10 thereof.

The advantages of such a two layer multi-filar structure can be understood with reference to FIG. 10. As noted above, this figure is a schematic cross-sectional view of the drive shaft of FIG. 2 taken along lines 10—10. This view would obviously be much more complicated if the spiral pattern formed by the distally increasing diameters of the wire turns of the outer layer 50 would be shown. FIG. 10, though, essentially represents the shape of the face of such a cross section, simplifying the drawing for purposes of discussion.

As seen in FIG. 10, the entire cross-sectional area of the outer layer 50 is made up from the thickness of a single wire strand. This requires that all of the torsional force delivered by the outer layer 50 be delivered through that single strand. The cross-sectional area of the inner layer 40 is fairly evenly divided between the three wire strands 41, 42 and 43. This means that the torsional force being delivered through the inner layer at any given point along its length is being divided substantially equally between the three wires, reducing the load on each individual wire. A majority of the torque can be delivered through the inner layer without unduly sacrificing flexibility of the drive shaft, thereby permitting the shape of the enlarged diameter segment of the outer layer to be optimized for tissue removal without needing to focus on the ability of the outer layer to deliver torque.

As noted above, the present invention also provides a method for forming a drive shaft for driving an operational element of a medical device. In accordance with this method, an inner helical coil 40 is formed by winding a plurality of wires 41, 42 and 43 about a forming mandrel. The wires may be of any suitable size or material. Typically, though, all of the wires of the Inner layer will be formed of substantially the same material and have substantially the same diameter and cross-sectional shape.

The diameter and material of the wires used in forming the inner helical coil will obviously depend to a large extent on the diameter of the vessels in which the drive shaft is to be used and the amount of torque which needs to be delivered. For example, for a drive shaft 20 used in connection with a rotational atherectomy device such as that illustrated in FIG. 2 (discussed in greater detail below) and has a maximum diameter of its enlarged diameter intermediate segment of about 2 mm, three round stainless steel wires, each having a diameter of between about 0.002 inches and about 0.008 inches, will typically be used, with diameters in the range of about 0.003–0.006 inches being believed to be most preferable.

Each of the wires 41–43 of the inner layer 40 is shown as being generally round in cross section. Other shapes can be used, though, as implied above. Wires for use in medical devices can be commercially purchased with different cross-sectional shapes, such as flattened rectangular shapes, ovals, etc. Use of flattened rectangular wire (typically with rounded corners) can provide a drive shaft with greater torsional strength than would a round wire of the same height.

As noted above, the wires 41, 42 and 43 are wound about a mandrel to produce the inner helical coil 40. The use of mandrels to form multi-filar helical coils is well known in the art and need not be discussed in detail here. Machines for winding helical coils using mandrels are readily commercially available. One advantage of a helical coil formed using a mandrel is that the manufacturer can fairly precisely control the dimensions of the resulting coil. Although the inner diameter of the final coil will tend to be slightly larger than the outer diameter of the forming mandrel, the spring-like expansion of the coil on the mandrel is highly predictable and yields very reproducible results for a given type of wire.

Maintaining precise control over the dimensions of the inner helical coil 40, and particularly the lumen 48 of that coil, is particularly important in a drive shaft of the invention. As noted above, the lumen 48 of the inner helical coil is adapted to receive a guide wire therein so the drive shaft can be rotated about the guide wire. If the inner diameter of the inner helical coil were to vary substantially, it could cause the drive shaft to lock down on the guide wire received in the lumen, causing the device to malfunction. Although mandrel-less coil forming techniques are known (and are discussed below), such mandrel-less coil forming techniques generally do not yield the same degree of precision as can be achieved with mandrel-based coil winding techniques. Accordingly, using a mandrel-less coil forming machine for the inner helical coil 40 could yield a much less consistent product and significantly more quality control rejections. In addition, commercially available mandrel-less coil forming machines are not designed to manufacture the multifilar helical coils preferred in the inner layer 40 of FIG. 2, for example.

The diameter of the outer layer is fairly important, but need not be as precisely controlled as is the diameter of the lumen 48 of the inner helical coil 40. It is possible to form the outer layer 50 over an appropriately shaped mandrel. In accordance with the present invention, however, utilizing a mandrel-less forming machine to form the outer helical coil 50 Is preferred. When the device is assembled, the inner layer 40 will be disposed between the outer layer 50 and the guide wire received in the lumen 48 of the drive shaft. As explained above, when the drive shaft is rotated, the inner helical coil 40 will tend to expand while the outer helical layer will tend to contract. Since the coils are designed to urge against one another (at least when the drive shaft is rotated), the outer layer 50 will limit the radial expansion of the inner layer 40 while the inner layer will limit the radial contraction of the outer layer. So long as the lumen 48 of the inner helical coil is appropriately sized to avoid locking down on the guide wire when the drive shaft 20 is rotated, the exact diameter of the outer layer of the drive shaft is likely to be less critical.

In order to enhance the flexibility of manufacturing the outer layer, it is preferred that a mandrel-less coil forming machine be used. Machines utilizing spring coiling technology are capable of coiling wires without the use of a mandrel. Commercially available machines utilizing this technology, such as machines available from WMC WAFIOS Machinery Corp. of Branford, Conn. (affiliated with WAFIOS Machinenfabrik GmbH & Co. of Reutlingen, Germany), typically include computer controllers which permit a user to vary the diameter of a coil along its length.

Use of these machines is facilitated by using a single wire strand, as opposed to multiple wire strands, in forming the outer helical layer. The precise dimension of this wire can be varied fairly widely. It may be desirable, though, to make the outer helical coil 50 of a wire having a different diameter or cross-sectional height than that of the wires 41–43 of the inner helical coil 40. For example, if the inner helical coil is made from 0.004 inch diameter wires, the outer helical coil may be made from a single 0.005 inch diameter wire. The precise diameters of these wires can be varied as necessary to achieve a specific design objective.

The unique structure of the present invention yields a number of surprising advantages. First, the method of the present invention gives one a great deal of flexibility in selecting an outer shape of the drive shaft to meet specific design objectives while maintaining precise dimensions in those areas of the drive shaft where dimensions are critical.

Even so, the drive shaft can be made relatively easily and with minimal quality assurance losses. In particular, forming the inner helical coil 40 on a mandrel yields very precise control over the diameter of the lumen 48. At the same time, utilizing a mandrel-less forming technique to form the outer helical coil 50 greatly enhances manufacturing ease and flexibility, permitting the diameter of the outer layer to be varied within a wide range of parameters without introducing substantial manufacturing problems.

Second, the present invention utilizes the best properties of each of the inner and outer helical coils 40, 50. The multi-filar inner helical coil 40 can be used to transmit the majority of the torque of the drive shaft. The multi-filar mandrel-formed construction of this layer greatly enhances torque delivery, as explained above, while maximizing precision of the diameter of the lumen 48 to improve system reliability. The outer helical coil 50 need not transmit as much torque and can be used to achieve other design objectives. For example, In the atherectomy devices shown in FIGS. 2–8 and 10–16, the shape of the outer helical coil can be varied fairly readily to produce an enlarged diameter segment (30 in FIG. 2) which is very stable in atherectomy procedures.

Once the inner and outer helical coils (40 and 50, respectively) are formed in their respective fashions, they can be assembled into a completed drive shaft. In so doing, the inner helical coil 40 is placed in the lumen of the outer helical coil 50. If so desired, these two coils may be bonded to one another at one or more positions along their length to minimize any relative dimensional changes (such as any differential changes in length which may occur as the coils expand or contract). For example, two mechanical bonds 36, 36 are shown in the drive shaft 20 of FIG. 2, with one such bond being positioned at the distal end of the intermediate segment and the other being positioned at the proximal end of the intermediate segment. These bonds can be formed in any suitable fashion, such as by using a solder or braze joint.

When the inner helical coil 40 is inserted into the lumen of the outer helical coil 50, care should be taken to maintain the proper orientation of the turns of these respective coils. In particular, the direction of the winding of one of these coils should be opposite that of the other coil. Both the inner and outer helical coils may then be attached to a common driver (which may be retained in the housing of the handle portion 10 of the device shown in FIG. 1, for example). The Inner and outer coils of the drive shaft should be attached to this driver such that when the driver is turned in a predetermined direction, the outer layer will tend to radially contract and the inner layer will tend to radially expand. As noted above, the inner and outer helical coils of the rotating drive shaft thus urge against one another and prevent the inner and outer diameters of the drive shaft from changing to such an extent that the drive shaft locks down on the guide wire or locks up against the lumen of the catheter.

A drive shaft in accordance with this embodiment of the invention is believed to be suitable for rotating a variety of operational elements. For example, a rotary blade can be attached to the distal end of the drive shaft to enable it to be used in a thrombectomy procedure. The illustrated embodiments of the present invention, though, are particularly useful in rotational atherectomy devices.

Turning to FIG. 2, the drive shaft 20 is formed of an Inner helical coil 40 received in an outer helical coil 50, generally as outlined above. The drive shaft generally comprises a proximal segment 22, a distal segment 24 and an enlarged diameter intermediate segment 30 disposed between the proximal and distal segments. In order to improve stability of the drive shaft and to minimize any problems associated with changes in length in the coils 40, 50 when they are rotated, the coils may be bonded to one another by bonds 36, 36 positioned at opposed ends of the enlarged diameter segment 30. As noted above, these bonds can be formed of any suitable materials, including solder or braze joints.

Optimally, a distal portion of the proximal segment 22 of the drive shaft 20 is encased in a thin, flexible, low friction coating or sheath 23. In a preferred embodiment, the coating or sheath 23 is sufficiently long so that its proximal end remains disposed inside the catheter (13 in FIG. 1) even when the drive shaft 20 is fully advanced distally with respect to the catheter. A heat shrinkable polytetrafluoroethylene tubing has been found to work well as such a sheath 22, but this sheath or coating may be made from any suitable material.

The enlarged diameter segment 30 includes a proximal portion 32 and a distal portion 34. In the embodiment shown in FIGS. 2 and 3, the outer layer of the intermediate segment 30 of the drive shaft 20 has a diameter that gradually increases distally through the proximal portion 32 and gradually decreases distally through the distal portion 34. It is worth noting that the rate of change of the diameter of the outer helical coil 50 is different in the proximal portion 32 than it is in the distal portion 34. In the preferred embodiment illustrated in FIG. 2, the outer helical coil in the distal portion 34 of the enlarged diameter segment 30 defines a convex, almost parabolic outer shape. The precise shape of the distal portion 34 can be varied as desired to provide the desired tissue removal profile.

The wire turns of the proximal portion 32 of the intermediate enlarged diameter segment 30 have diameters that gradually increase distally at a generally constant rate. This yields a proximal segment which is generally in the shape of a cone. The advantages of this conical shape will be discussed in more detail below. At least part of the enlarged diameter segment 30 (preferably most or all of the distal portion 34 thereof) includes an abrasive external surface to define an abrasive segment of the drive shaft 20. In a preferred embodiment, this abrasive external surface is formed by applying an external coating of an abrasive material 38. The abrasive material may be any suitable material, such as diamond chips, fused silica, titanium nitride, tungsten carbide, aluminum oxide, boron carbide, or other ceramic materials. Preferably, the abrasive material is comprised of diamond chips (or diamond dust particles) attached directly to the wire turns of the outer helical layer 50 by a suitable binder 39. Such attachment may be achieved using a variety of well known techniques, such as conventional electroplating or fusion technologies, such as those set forth in U.S. Pat. No. 4,018,576.

The diameter of the inner helical coil 40 is not varied along the length of the drive shaft 20 shown in FIG. 2. Instead, this coil 40 is maintained at a substantially constant diameter so that it can serve as an effective bearing and structural support against a guide wire (not shown) received therein during operation.

The spacing of the wire turns along the length of the inner helical coil 40 can be kept substantially constant along the coil's length, as well. In the embodiment shown in FIG. 2, though, the spacing of the wires 41–43 in the enlarged diameter segment 30 of the drive shaft is different from that employed in either the distal segment 24 or the proximal segment 22. More specifically, the wires 41, 42 and 43 define a wire group 44 which is used to form the inner helical coil. In both the proximal segment 22 and the distal segment 24, adjacent turns of the wires are positioned immediately adjacent to one another, as are adjacent turns of the wire group. (These wire turns may truly abut one another. As suggested in the drawings, though, there is typically some slight spacing between adjacent turns inherently introduced in forming a coil about a mandrel. These spaces are typically quite small, though, and usually are less than 10 μm.) In the intermediate segment 30, the adjacent wires 41–43 remain immediately adjacent to one another and may even abut one another. However, a space is preferably left between adjacent turns of the wire group 44, yielding a helical gap 46, which optimally extends essentially along the entire intermediate segment of the inner helical coil. It has been found that a helical gap 46 having a width of about 25–30 μm will work well.

Figure 4:
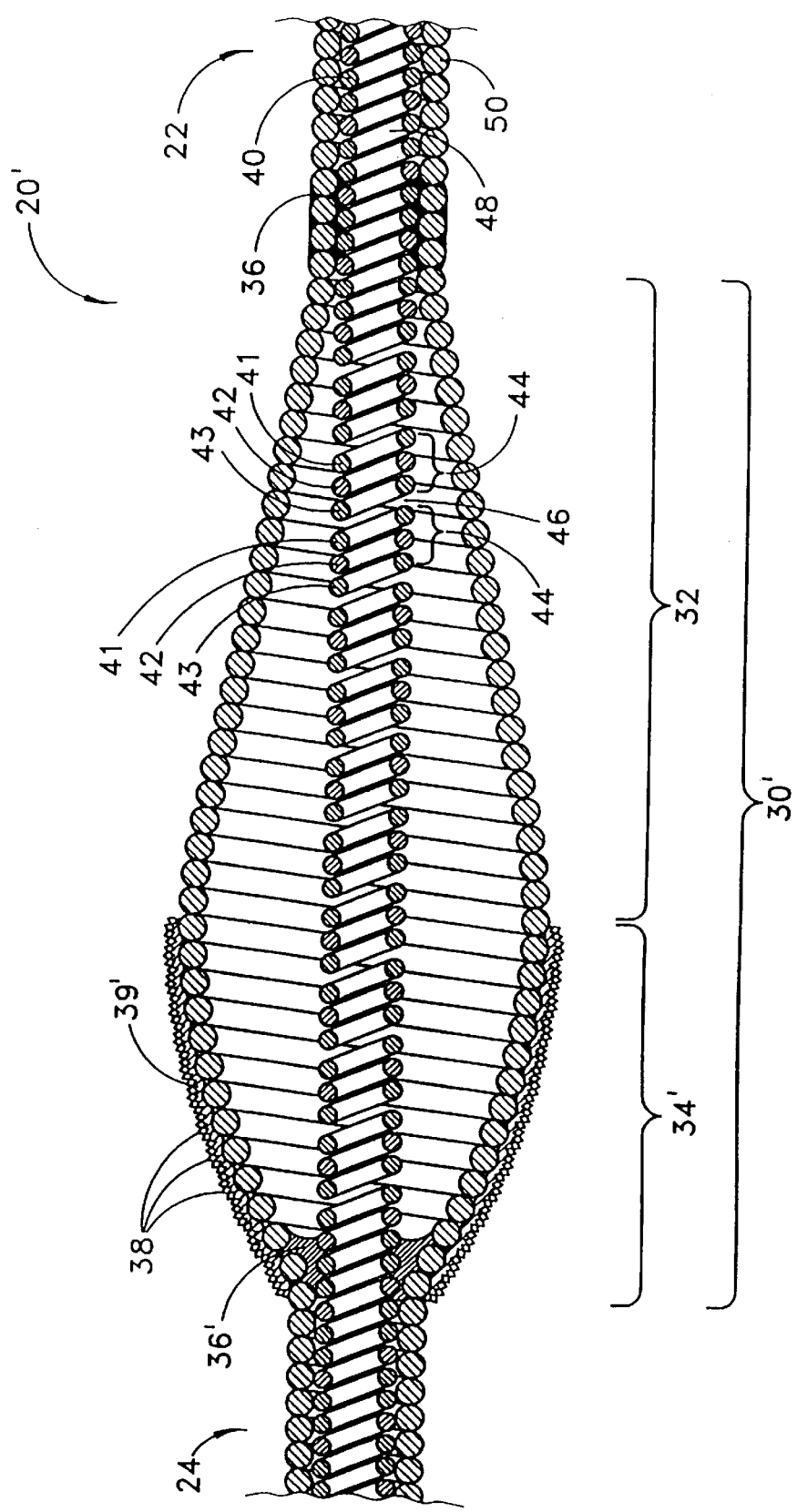
FIG. 4 is a broken-away, longitudinal cross-sectional view of the enlarged diameter segment of the drive shaft of an alternative embodiment of an atherectomy device of the invention.

FIG. 4 illustrates an abrasive drive shaft 20' which, in most respects, is similar to the drive shaft 20 illustrated in FIG. 2. Like reference numerals have been used in FIGS. 4 and 2 to indicate elements which are substantially the same, both functionally and structurally, in both designs. For those elements in FIG. 4 which provide similar functions to elements in FIG. 2 but differ structurally, like reference numbers are also used, but bear a prime. For example, the proximal portion 34' in FIG. 4 serves much the same function as does the proximal portion 34 in FIG. 2, but it has a different structure.

Much like the drive shaft of FIG. 2, the modified drive shaft 20' in FIG. 4 includes a proximal segment 22, a distal segment 24 and an enlarged diameter segment disposed between those two segments. The proximal and distal segments of the two drive shafts can be substantially Identical. Similarly, the inner helical coil 40 can be substantially the same in both of the drive shafts 20' and 20, and the proximal portion 32 of the enlarged diameter segment may also be essentially the same in both embodiments.

The primary differences between the two designs 20 and 20' lie in the area f the distal portion 34' of the enlarged diameter segment 30'. The distal portion 34 illustrated in FIG. 2 shows the abrasive 38 bonded to the wire turns forming the distal portion 34, but the wire turns are not bonded directly to one another. In the distal portion 34' in FIG. 4, though, the wire turns of the distal portion 34' are bonded to one another along the length of the distal portion. The same binder 39' which bonds the adjacent wire turns to one another may also be used to bond the abrasive material 38 to the distal segment 34' to yield the abrasive segment of the drive shaft. The binder 39' may be of the same type and applied in much the same fashion as the binder 39 shown in FIG. 2 and discussed above.

It is to be understood that wire turns may be bonded to one another along only part of the distal portion 34', thus making the abrasive segment shorter than the length of the distal portion 34'. The same is true for the relative lengths of the distal portion 34 of FIG. 2 and its abrasive segment.

Bonding adjacent turns of the wire to one another will obviously yield a stiffer abrasive segment because adjacent turns of the wire are not able to move with respect to one another as they are in the distal portion 34 shown in FIG. 2.

Bonding adjacent wire turns of the abrasive segment to one another, though, has two advantages. First, the wire turns of the abrasive segment do not fall out of alignment with one another when the enlarged diameter intermediate segment 30' is bent around even a tight curve. While the wire turns of the distal segment 34 shown in FIG. 3 remain in alignment with one another, they likely will start to fall out of alignment with one another if the enlarged diameter segment 30 of that design were bent around a tighter curve. The wire turns of the distal segment 34' in FIGS. 4 and 5, though, are physically bonded to one another and simply cannot fall out of alignment. Second, in a commercial manufacturing operation, it is much easier to bond adjacent turns of the wire together while bonding the abrasive material to the wire than it is to bond the abrasive material to the wire without bonding the wire turns to one another.

If the bond 36' shown in FIG. 4 were to remain in the same place as the bond 36 at the distal end of the enlarged diameter segment 30 in FIG. 2, this bond would even further extend the length of the relatively stiff portion of the drive shaft 20'. In order to minimize the length of this stiff portion, the bond 36' in the drive shaft 20' of FIG. 4 is positioned generally within the confines of the more rigid distal portion 34'. This still permits the inner helical coil 40 and outer helical coil 50 to be bonded to one another at appropriate locations adjacent opposite ends of the enlarged diameter segment 30' without unduly extending the length of the relatively inflexible portion of the drive shaft 20'.

Figure 3:
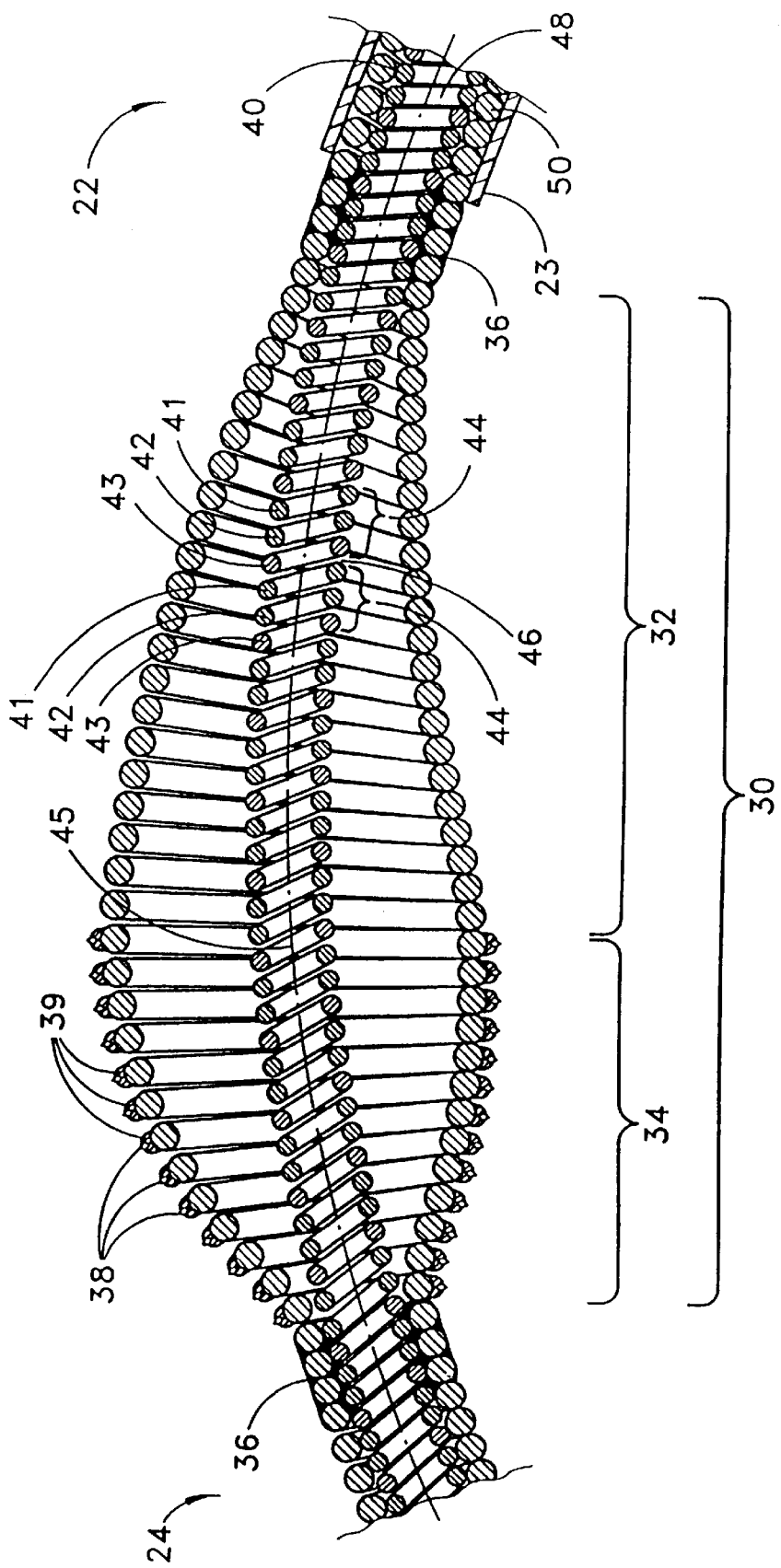
FIG. 3 is a broken-away, longitudinal cross-sectional view of the drive shaft of the atherectomy device of FIG. 2 depicted in a curved configuration.
Figure 5:
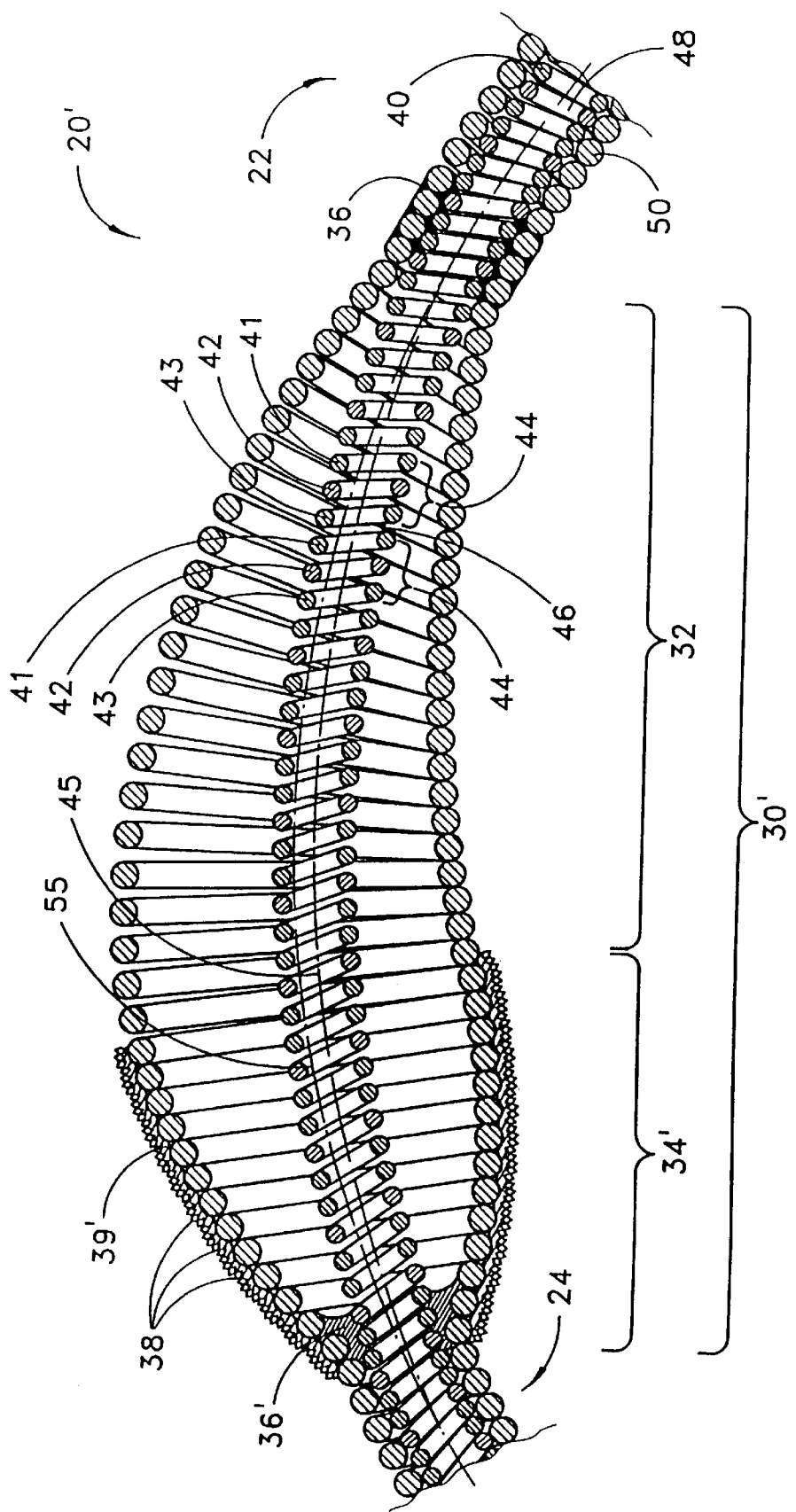
FIG. 5 is a broken-away, longitudinal cross-sectional view of the drive shaft of the atherectomy device of FIG. 4 depicted In a curved configuration.
Figure 8:
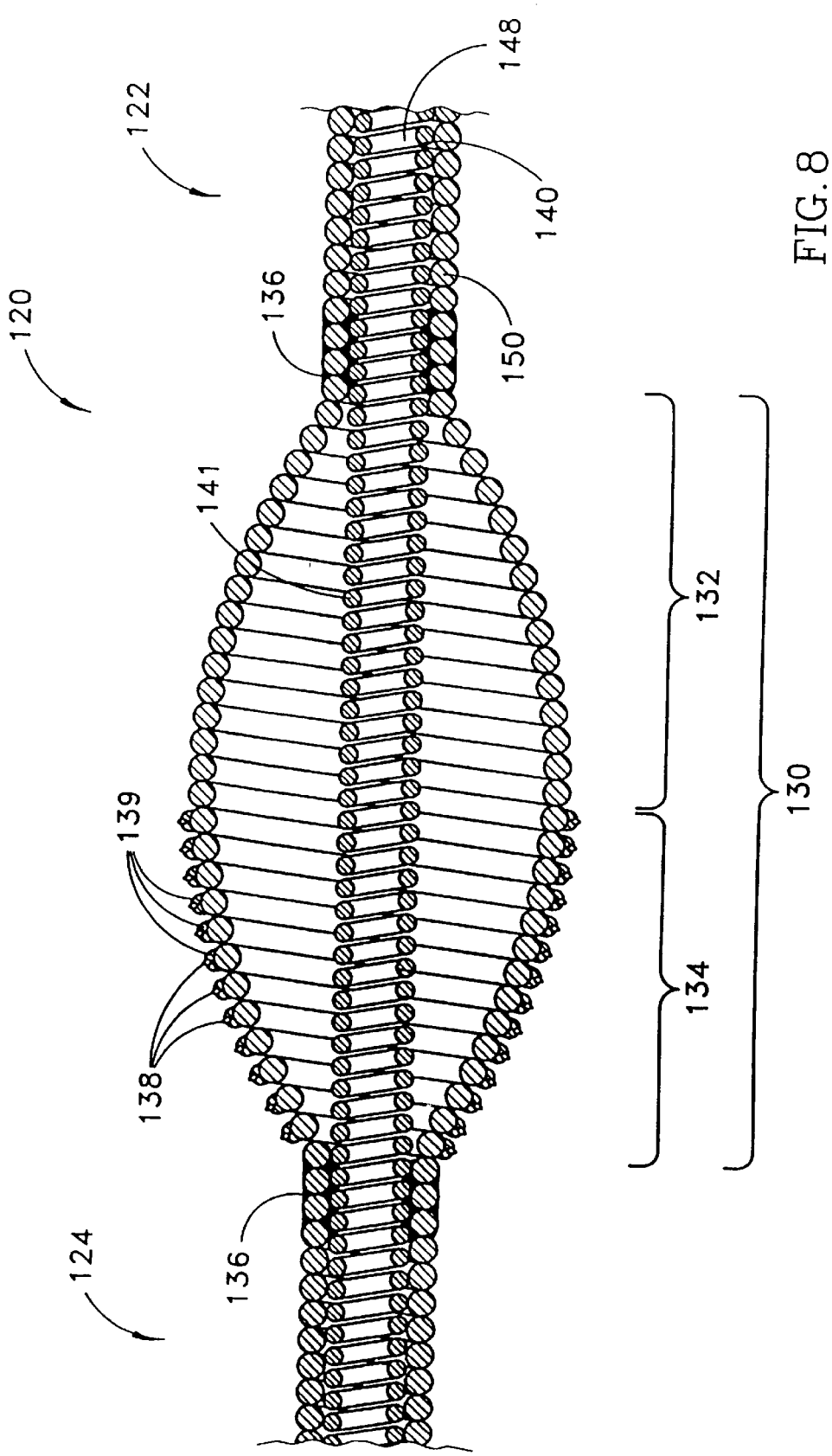
FIG. 8 is a broken-away, longitudinal cross-sectional view of the enlarged diameter segment of the drive shaft of a prior art atherectomy device.
Figure 9:
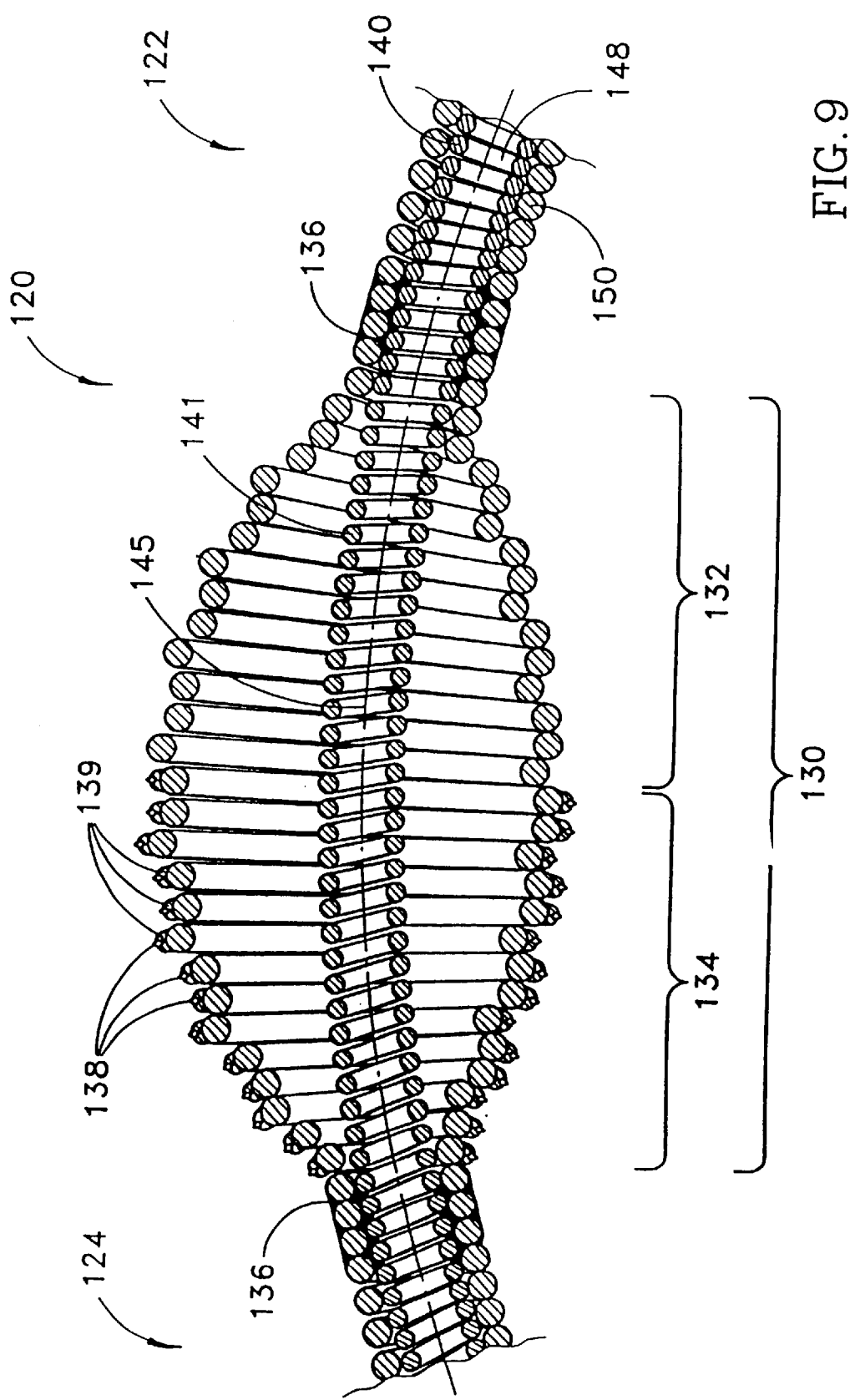
FIG. 9 is a broken-away, longitudinal cross-sectional view of the drive shaft of the prior art atherectomy device of FIG. 8 depicted in a curved configuration.

FIG. 8 depicts a portion of a drive shaft 120 for a rotational atherectomy device similar to that described in U.S. patent No. 5,314,438 (Shturman), the teachings of which were incorporated by reference above. In this drawing, reference numbers similar to those used in FIGS. 2 and 4 are employed to designate functionally similar elements, but with an increase in the reference number by 100 (e.g., drive shaft 120 in FIG. 8 is functionally similar to drive shaft 20 in FIG. 2). In FIGS. 2, 4 and 8, the enlarged diameter segments (30, 30' and 130, respectively) are shown in a generally straight (i.e., "at rest") configuration. FIGS. 3 and 5 illustrate the drive shafts of FIGS. 2 and 4, respectively, bent into a curved configuration. Similarly, FIG. 9 illustrates the drive shaft 120 of FIG. 8 in a curved configuration. The differences in performance characteristics schematically illustrated in these drawings are particularly instructive.

Notice that in FIG. 9 (which depicts the drive shaft 120 of the prior art atherectomy device), adjacent windings in the outer layer 150 of the enlarged diameter segment 130 have slipped past one another, coming out of smooth alignment. By comparison, the enlarged diameter intermediate segments 30 and 30' maintain a relatively smooth outer surface, even when bent as shown in FIGS. 3 and 5, respectively. By providing the proximal portion 32 of the enlarged diameter segment 30 of the drive shaft 20 or 20' with a generally conical shape, the wire turns tend to stay in alignment as this portion of the drive shaft is bent around a curve. Alignment of the wire turns in FIGS. 3 and 5 can easily be compared to the misalignment of the wire turns in FIG. 9. This graphically illustrates the advantages of the conical shape employed in FIGS. 2–5 over the prior art design shown in FIGS. 8 and 9.

As noted above, substantially all of the adjacent wire turns of the distal portion 34' of the drive shaft 20' of FIGS. 4 and 5 are attached to one another with a binder 39'. This makes the outer layer along the distal portion 34' significantly less flexible than the outer layer along the proximal portion 32, affecting the manner in which the outer layer 50 curves. The gap 46 between adjacent turns of the wire group 44 in the inner helical coil 40, though, permits this coil 40 to flex fairly freely within the confines of the outer helical coil 50 between the two bonds 36', 36. It is believed that providing spaces between at least some adjacent wire turns is important to optimize flexibility of the enlarged diameter segment. In the illustrated embodiment, the spaces have been provided as a helical gap 46 between adjacent turns of the wire group 44, but it may be possible to provide sufficient spacing by other means, such as by spacing individual wire turns from one another. Most importantly, the enhanced ability of the inner helical coil 40 to float within the confines of the outer helical coil 50, provided by the helical gap 46, is believed to substantially improve operation of the drive shaft 20 when the enlarged diameter segment is bent around a curve.

Each of FIGS. 3 and 9 illustrate a drive shaft having an enlarged diameter segment with a maximum diameter of about 2 mm, bent into a curved configuration with a longitudinal axis (45 in FIG. 3, 145 in FIG. 9) having a radius of curvature of about 10 mm. In the drive shafts of FIGS. 3 and 9, the axis of the inner helical coil and the axis of the outer helical coil substantially coincide with one another (jointly identified as 45 in FIG. 3 and as 145 in FIG. 9).

FIG. 5 also illustrates a drive shaft having an enlarged diameter segment with a maximum diameter of about 2 mm, but the axes of the inner and outer helical coils do not coincide with one another in this drawing. Since the outer helical coil 50 is rigid along substantially all of the distal portion 34' of the enlarged diameter segment while the inner coil 40 is not, the axis 55 of the outer coil will not always coincide with the axis 45 of the inner coil. Instead, through a significant range of curvatures, the axis 55 of the outer coil will be spaced above the axis 45 of the inner coil, as shown in FIG. 5. (The axes of these two coils will continue to generally coincide with one another in the proximal 22 and distal 24 segments of the drive shaft.) This difference in position of the respective axes of the inner coil 40 and the outer coil 50 will vary as the radius of curvature of the drive shaft is changed. As shown in FIG. 5, the difference is quite noticeable when the radius of curvature of the outer helical coil (i.e. the radius of curvature of the axis 55) is about 6 mm, as illustrated in the drawings. At larger radii of curvature (i.e. when the drive shaft is bent less dramatically), the distance between the two axes 45 and 55 diminishes and becomes negligible at a radius of curvature of about 10 mm.

In addition, positioning a guidewire (not shown) in the lumen 48 of the drive shaft will affect the curvature of the inner helical coil 40 and, hence, the position of its axis 45 within the confines of the outer helical coil 50 of the enlarged diameter segment 30. Since guidewires currently used in rotational atherectomy procedures are stiffer than the fairly flexible inner helical coil 40, the combined guidewire and inner helical coil will not be able to float as freely within the confines of the outer helical coil as can the inner helical coil alone. Hence, when the drive shaft has been bent with a guidewire in the lumen 48, the distance between the two axes 45 and 55 will be smaller than when it is bent without a guidewire as shown in FIG. 5.

Figure 6:
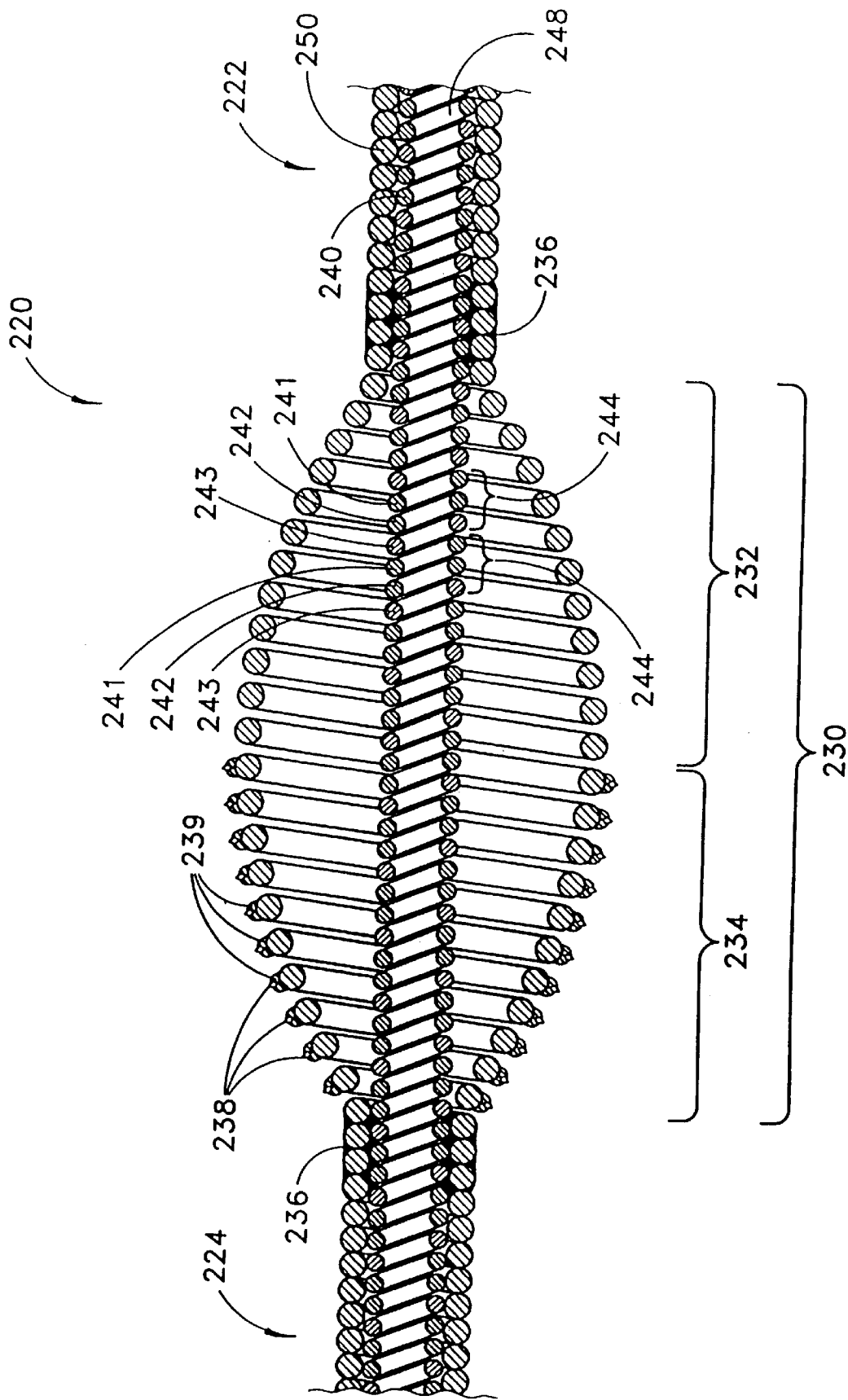
FIG. 6 is a broken-away, longitudinal cross-sectional view of the enlarged diameter segment of the drive shaft of another embodiment of the invention.

FIG. 6 illustrates yet another alternative embodiment of a drive shaft 220 for use in a rotational atherectomy device in accordance with the present invention. Once again, like reference numbers are used to refer to parts which perform substantially the same function as parts of the drive shaft 20 shown in FIG. 2, with the addition of 200 to the reference numbers.

Figure 7:
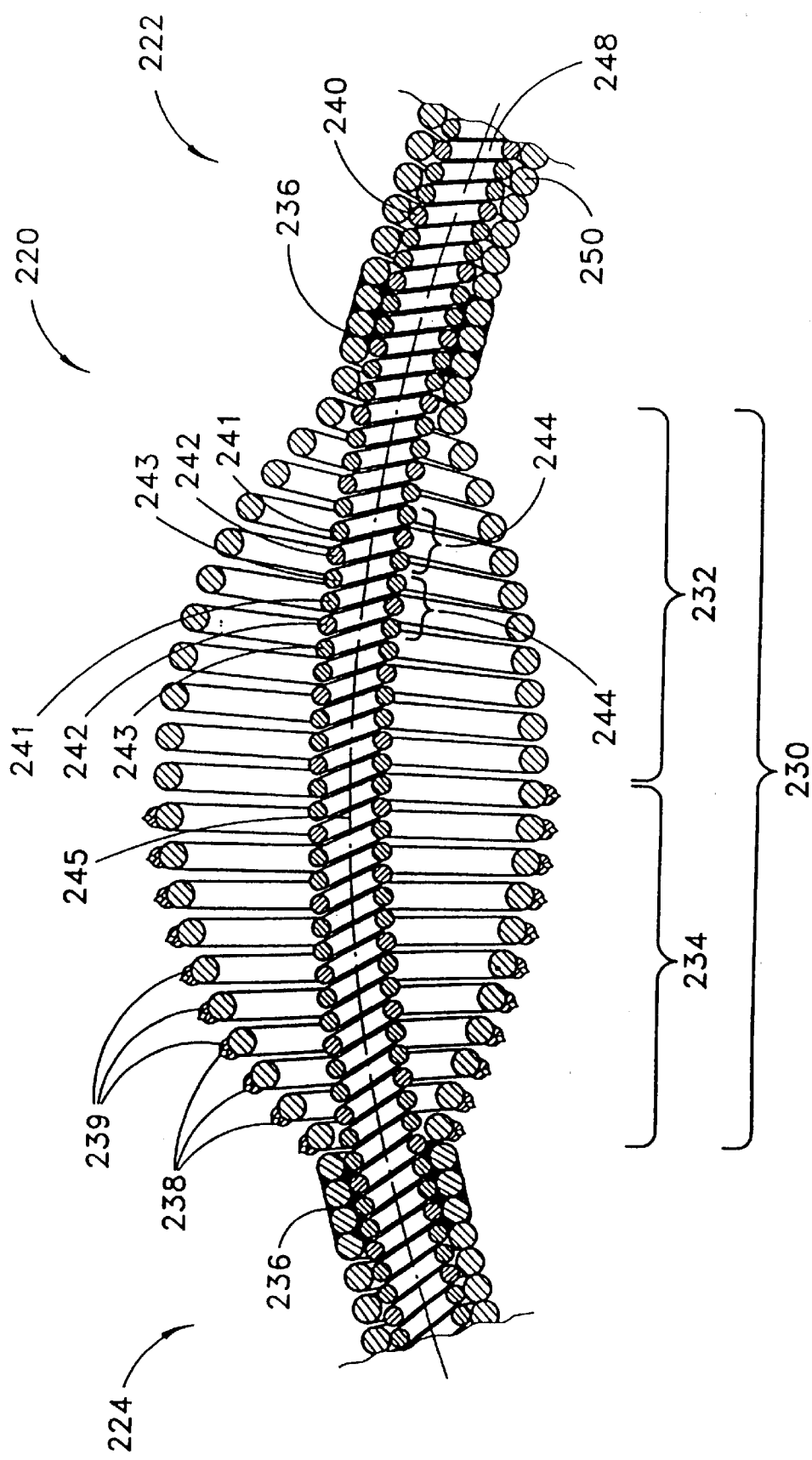
FIG. 7 is a broken-away, longitudinal cross-sectional view of the drive shaft of the atherectomy device of FIG. 6 in a curved configuration.

FIGS. 2 and 4 both show drive shafts wherein the wire turns of their respective proximal portions 32 of their enlarged diameter segments 30 and 30' have diameters which gradually increase distally at a generally constant rate, each forming generally the shape of a cone. The wire turns of the distal portions 34 and 34' form a generally convex, almost parabolic outer shapes, yielding asymmetrical profiles of the enlarged diameter segments 30 and 30'. The enlarged diameter segment 230 of the drive shaft 220 shown in FIG. 6, though, can have a more symmetrical appearance. In particular, the proximal portion 232 of the enlarged diameter segment 230 need not have the aforementioned conical shape in order to flex properly in use. As can be seen in FIG. 7, the drive shaft 220 of FIG. 6 when bent still yields a smooth outer profile without the misalignment of adjacent wire turns typified in FIG. 9.

The means by which the enlarged diameter segment 230 maintains this profile is different from the manner utilized in the drive shafts of FIGS. 2 and 4. Each of the enlarged diameter intermediate segments 30, 30' and 130 of FIGS. 2, 4 and 8, respectively, utilize an outer helical coil which is essentially bottomed out (i.e., wherein adjacent turns of the outer helical coil essentially abut against one another along the enlarged diameter intermediate segment). The drive shaft 220 of FIG. 6, though, provides spaces between adjacent turns of the outer helical coil 250 in the enlarged diameter segment 230. This spacing can be varied by controlling the pitch of the wire during the process of forming the outer helical coil. Obviously, the diameter of the coil affects the pitch needed to achieve appropriate spacing between adjacent wire turns.

The relative spacing of the adjacent wire turns in the outer helical coil of the enlarged diameter segment 230 is important to provide optimal operation of the drive shaft. The spacing between adjacent wire turns of the outer helical coil 250 in the proximal portion 232 of the enlarged diameter segment 230 desirably gradually increases distally. Conversely, the spacing between adjacent wire turns of the outer helical coil 250 in the distal portion 234 of the enlarged diameter segment 230 desirably gradually decreases distally. For an enlarged diameter segment 230 having a maximum diameter of about 2 mm, a maximum spacing between adjacent wire turns of the outer helical coil from about 25 $\mu$m to about 30 $\mu$m has been found to work well.

The cross sectional view of FIG. 6 appears to show a plurality of distinct gaps between adjacent wire turns. It should be recognized that these wire turns are actually formed from a single helically wound wire and, therefore, there is only a single helical gap. As the spacing between adjacent wire turns of the outer helical coil gradually increases in the proximal portion 232, the width of this helical gap gradually increases. As the spacing between adjacent wire turns of the outer helical coil gradually decreases in the distal portion 234, the width of this helical gap gradually decreases.

FIG. 7 shows the drive shaft 220 of FIG. 6 bent around a curve having a radius of curvature of about 10 mm. As shown in FIG. 7, the wire turns of the outer helical coil 250 do not fall out of alignment with each other when the enlarged diameter segment 230 of the drive shaft 220 is so bent. FIG. 9 shows the prior art drive shaft 120 of FIG. 8 bent around a similar curve. FIG. 9 demonstrates that the adjacent wire turns of the outer helical layer 150 along the enlarged diameter segment 130 are pushed out of alignment with one another when the drive shaft 120 of FIG. 8 is bent around such curve.

The enlarged diameter segment 130 in FIGS. 8 and 9 is very similar in most respects to the enlarged diameter segment 230 of FIGS. 6 and 7, except that the outer helical coil 150 of FIGS. 8 and 9 does not have the spacing employed in the outer helical coil 250 of FIGS. 6 and 7. The spacing between adjacent wire turns of the outer helical coil allows adjacent wire turns on the bottom of the enlarged diameter segment 230 (i.e., the side of the enlarged diameter segment having the smaller radius of curvature) to move toward one another while adjacent wire turns on the top of the enlarged diameter segment 230 (i.e., the side of the enlarged diameter segment having the larger radius of curvature) move farther apart from one another. Again, FIG. 7 demonstrates that sufficient spacing between adjacent turns of the outer helical coil 250 helps maintain the smooth profile of the enlarged diameter segment 230 even when this segment 230 is bent.

It is important to note that the structure of the inner helical coil 240 shown in FIG. 6 is a little different from that of the inner helical coil 40 shown in FIGS. 2 and 4. The drive shafts 20 and 20' of FIGS. 2 and 4 have an inner helical coil 40 which, along the enlarged diameter segment 30, has a helical gap 46 defined by adjacent turns of the wire group 44. Such a helical gap between adjacent turns of the wire group 244 is not necessary in the drive shaft 220 illustrated in FIGS. 6 and 7. Instead, the adjacent turns of the wire group 244 in the inner helical coil 240 are maintained essentially bottomed out along the entire length of the enlarged diameter segment 230. In each design, though, there is an elongate helical gap in either the inner helical coil or the outer helical coil along the enlarged diameter segment. In each of FIGS. 2 and 4, the outer helical coil is bottomed out while the inner helical coil is provided with an elongate helical gap 46; in FIG. 6, the inner helical coil is bottomed out while the outer helical coil is provided with an elongate helical gap. The presence of such an elongate helical gap in one layer, while the other layer remains bottomed out, permits the enlarged diameter segment to be flexed without losing its smooth outer shape while transmitting suitable torque to abrade atheromatous material.

Figure 11:
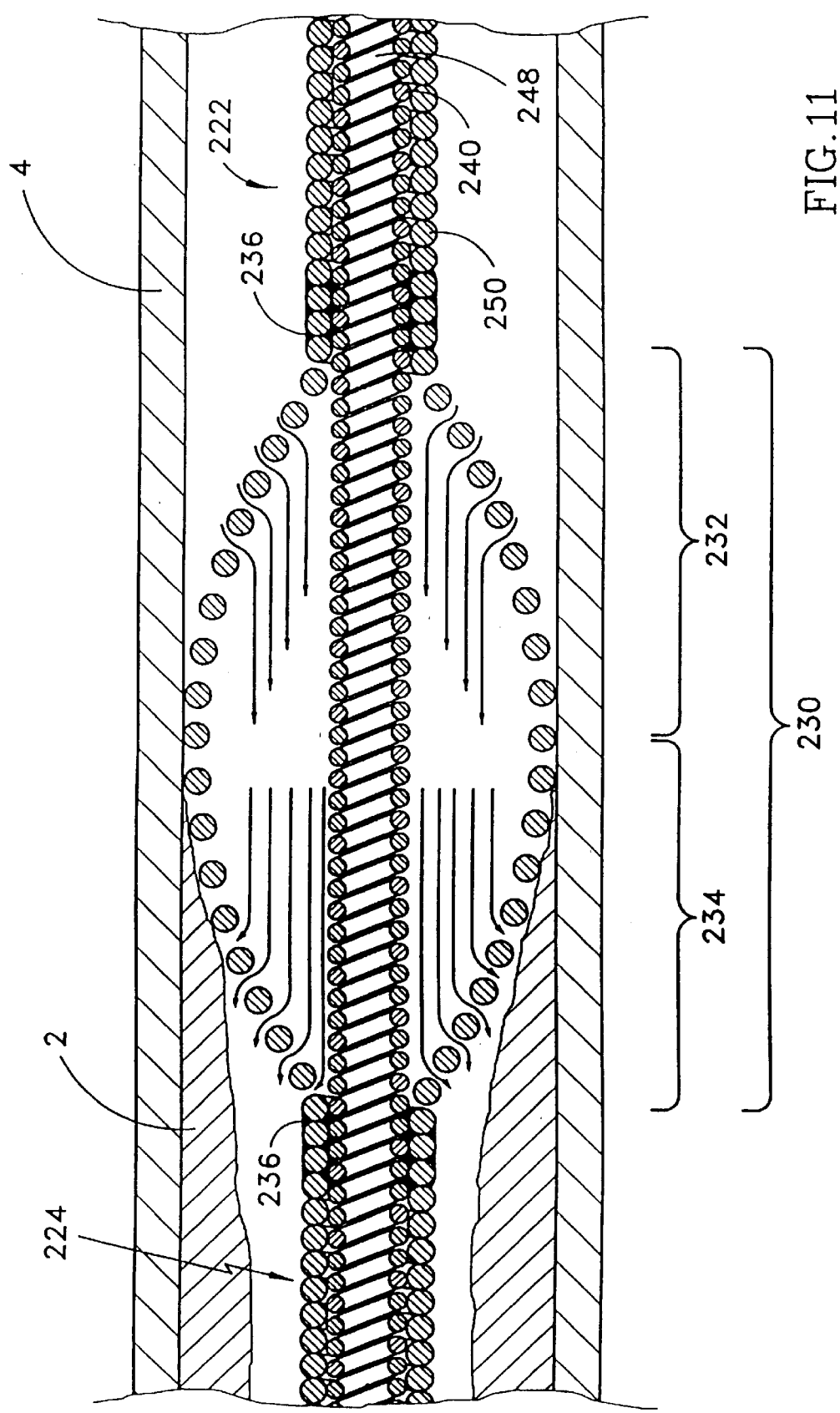
FIG. 11 is a schematic broken-away, longitudinal cross-sectional view of the drive shaft of the atherectomy device of FIG. 6 placed within a patient's vessel.

FIG. 11 schematically illustrates a build-up of atheromatous material 2 along the lumen of a patient's artery 4. The enlarged diameter segment 230 of the drive shaft 220 (originally shown in FIG. 6) is shown in FIG. 11 in contact with the atheromatous material 2 so that the abrasive material of the distal portion 234 can abrade the atheromatous material.

In prior art designs, the abrasive portion of the device typically precludes the flow of blood therethrough. For example, in Auth's design, a solid burr is utilized. In the prior art drive shaft 120 shown in FIGS. 8 and 9 of the present application, the abutment of each of the wires against one another in the enlarged diameter segment will also effectively preclude the flow of fluids through the outer helical coil 150 in this segment. Accordingly, there is no ready path provided to permit blood in the artery 4 to flow from a position proximal of the enlarged diameter segment 130 to the other side of the atheromatous build-up while the device is in use.

FIG. 11 illustrates another advantage of the drive shaft 220 illustrated in FIG. 6. As illustrated schematically in FIG. 11, the drive shaft 220 permits blood or other fluids to flow through the enlarged diameter segment 230. This blood flow is schematically illustrated by arrows. (For purposes of clarity, the drawing in FIG. 11 has been simplified by omitting the abrasive material 238 as well as some of the lines representing the turns of the outer helical coil 250.) As indicated, fluid can flow through the gaps between adjacent turns of the outer helical coil 250 in the proximal portion 232 of the enlarged diameter segment. The fluid entering the enlarged diameter segment may then pass through the gaps between adjacent turns of the outer helical coil 250 in the distal portion 234 of the enlarged diameter segment, defining a path for fluid flow through the enlarged diameter segment.

Several of the drive shafts illustrated in Shturman's U.S. Pat. No. 5,314,438 (discussed above) include gaps in the enlarged diameter segments to facilitate ultrasound imaging (see, e.g., FIGS. 9–22 of that patent). As illustrated in that patent, the ultrasound imaging gap is only provided between two adjacent turns of the helical coil and, thus, the gap extends only for about a single turn of the helical coil. In addition, the gap is positioned generally along the middle of the enlarged diameter segment. Therefore, this ultrasound imaging gap Is located essentially at the largest diameter of the enlarged diameter segment of the drive shaft and the gap will be effectively occluded by atheromatous material or by the arterial wall itself when the drive shaft is used to reopen an atherosclerotically occluded artery.

In the embodiment shown in FIG. 11, though, the gap has a length equal to the length of essentially all turns of the outer helical coil 250 along the enlarged diameter segment. (This long gap appears to present multiple gaps in the cross sectional view of FIG. 11.) The long gap greatly improves fluid flow through the enlarged diameter segment 230. This fluid flow is advantageous for at least two reasons. First, it can allow blood to flow through the region being treated, allowing the operator to treat the underlying stenosis without having to block the flow of blood to anatomical structures supplied by the artery being treated and located downstream of the stenosis. Second, fluids passing through the enlarged diameter segment 230 will serve as both a cooling medium and a lubricant, helping minimize any heat which may build up due to the friction between the enlarged diameter segment 230 and the atheromatous material 2.

Figure 12:
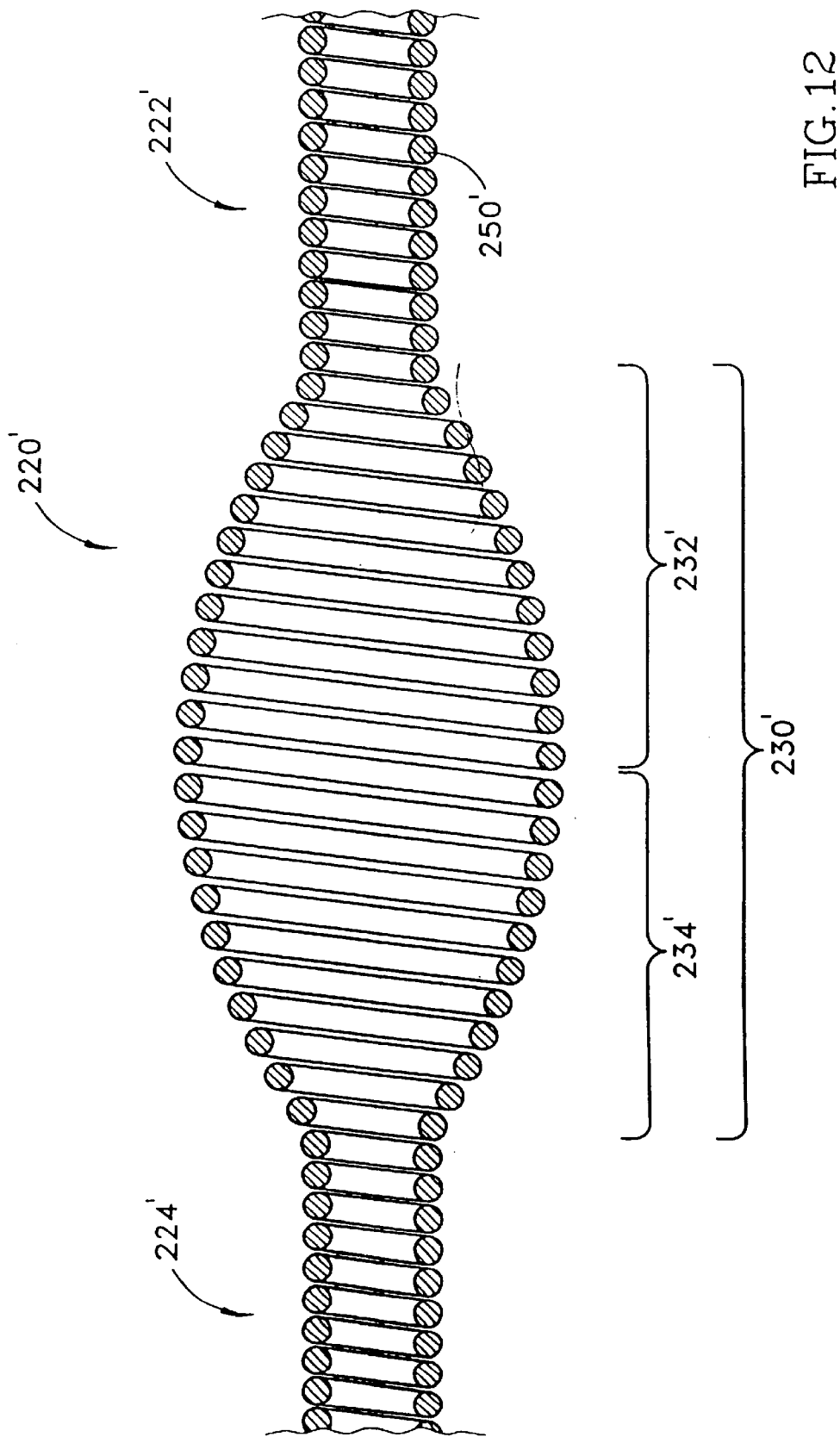
FIG. 12 is a broken-away, longitudinal cross-sectional view of the enlarged diameter segment of the drive shaft of a modified embodiment of the invention utilizing a mono-filar drive shaft.
Figure 13:
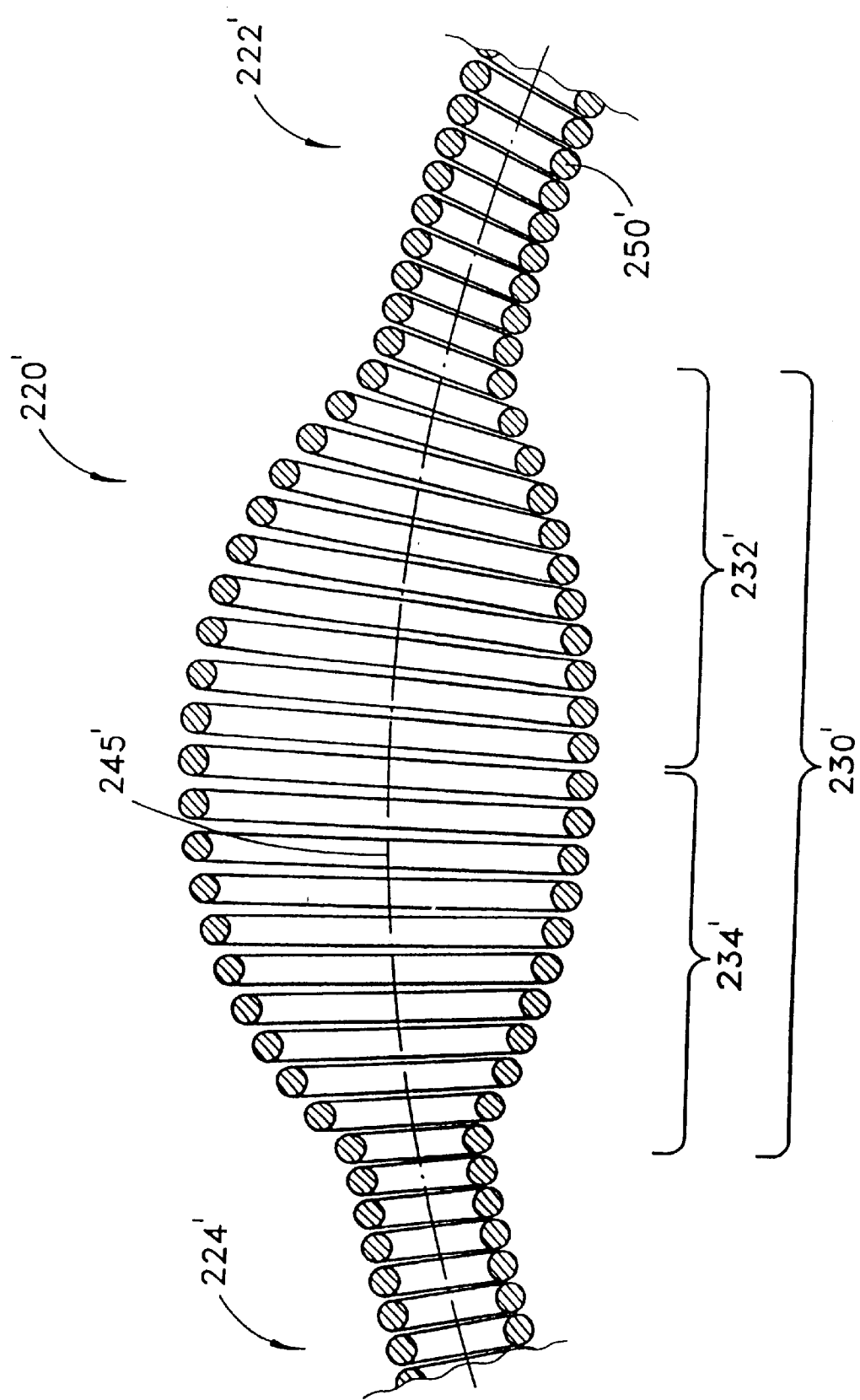
FIG. 13 is a broken-away, longitudinal cross-sectional view of the drive shaft of the atherectomy device of FIG. 12 depicted In a curved configuration.

FIGS. 12 and 13 illustrate another alternative embodiment of the invention. This drive shaft 220' is very similar to the drive shaft 220 illustrated In FIGS. 6 and 7. The drive shaft 220 includes both an outer helical coil 250 and an inner helical coil 240, as detailed above. In the embodiment of FIGS. 12 and 13, though, the drive shaft 220' includes only a single helical coil 250'. This helical 0 coil 250' is desirably formed of a single wire, i.e., this coil is desirably a monofilar coil. Like the outer layer 250 of the drive shaft 220 in FIGS. 6 and 7, the proximal portion 232' of the enlarged diameter segment 230' has wire turns which have diameters that gradually increase distally and spaces between adjacent wire turns which gradually increase distally. Conversely, the distal segment 234' has wire turns which have diameters that gradually decrease distally and spaces between adjacent wire turns which gradually decrease distally through the distal portion 234'.

As noted above, the primary difference between the drive shaft 220' in FIGS. 12 and 13 and the drive shaft 220 in FIGS. 6 and 7 is that the drive shaft 220' includes only a single coil 250'. The other advantages outlined above in connection with the earlier drive shaft 220 would continue to apply with respect to this modified design 220'. In particular, as illustrated in FIG. 13, the enlarged diameter segment 230' can be curved through an arc with minimal chance of having adjacent wire turns slip out of alignment with one another. (Compare FIG. 13 with the prior art device illustrated in FIG. 9.) Additionally, fluid can flow relatively freely through the enlarged diameter segment 230' in much the same fashion as discussed above in connection with the enlarged diameter segment 230 shown in FIG. 11.

Figure 14:
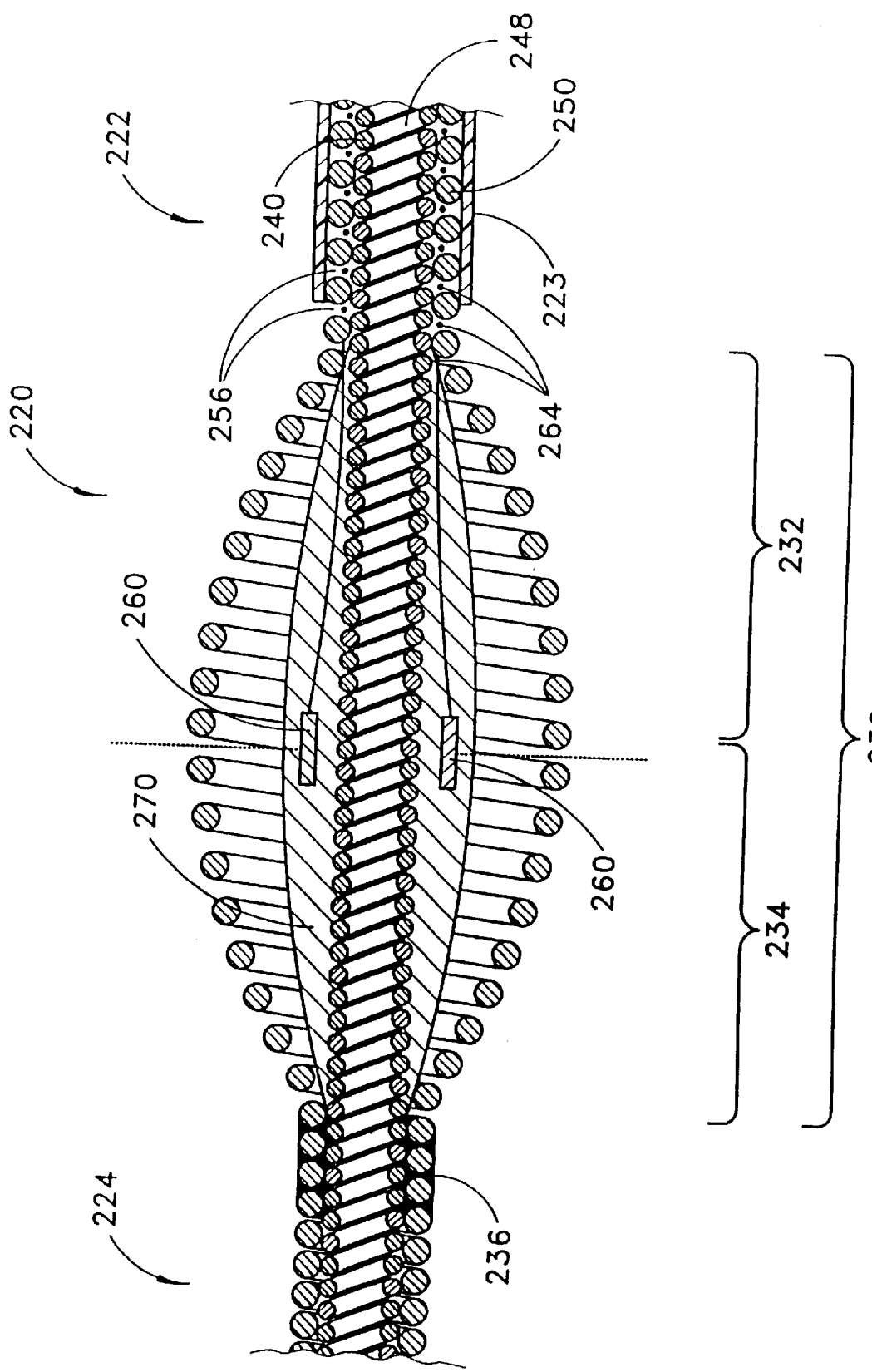
FIG. 14 is a broken-away, longitudinal cross-sectional view of the enlarged diameter segment of a modified embodiment of the invention, similar to FIG. 6, with the addition of ultrasound imaging transducers carried within a flexible bushing.
Figure 15:
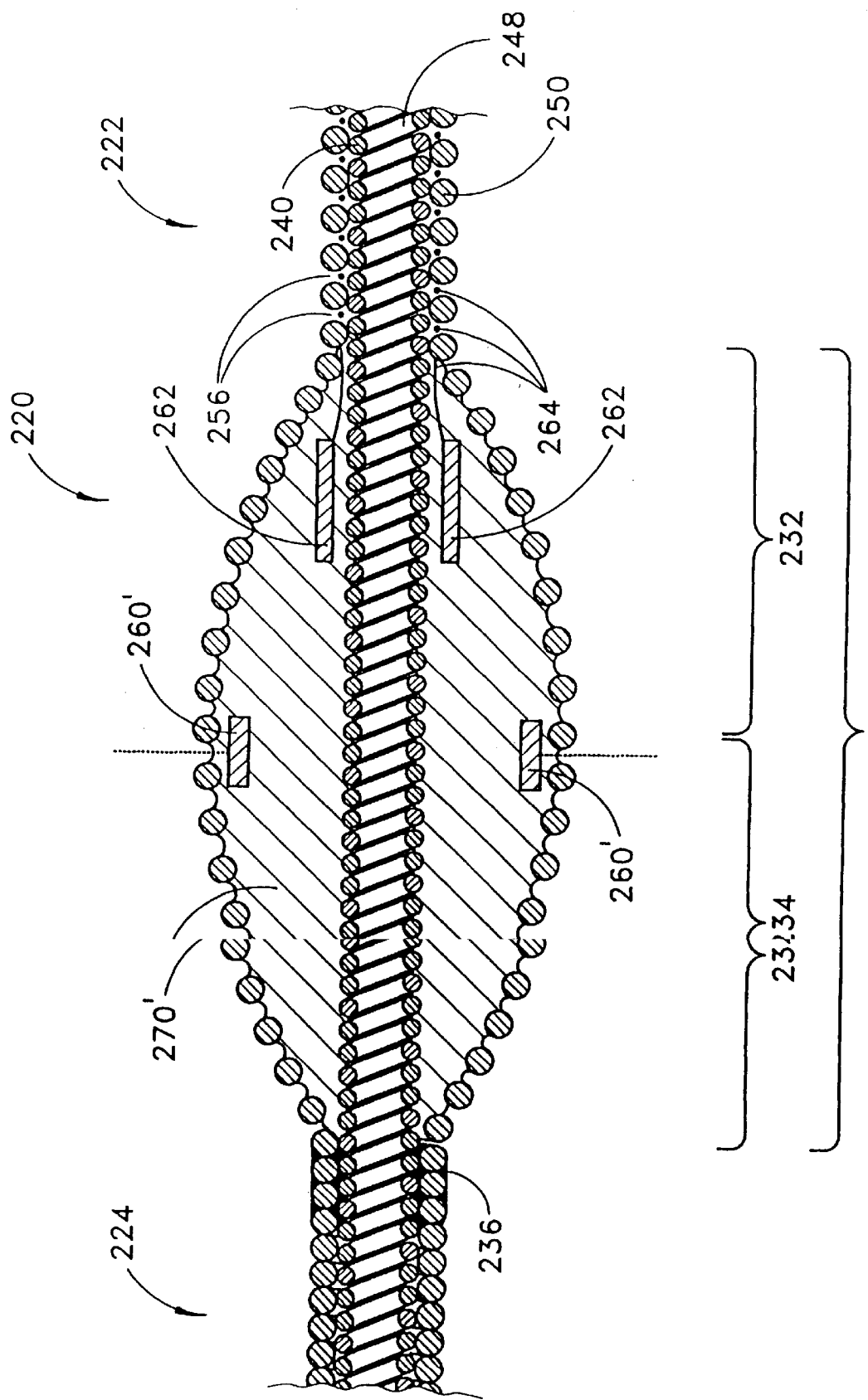
FIG. 15 is a broken-away, longitudinal cross-sectional view of the enlarged diameter segment of another modified embodiment of the invention wherein ultrasound imaging transducers and processors are retained within a larger diameter bushing.

FIGS. 14 and 15 illustrate two possible modifications of the drive shaft 220 shown in FIG. 6. A majority of the structural features of the drive shaft 220 remain the same as those illustrated in the earlier drawing, so like reference numbers are used in FIGS. 14 and 15. The drive shafts shown In FIGS. 14 and 15 differ from the drive shaft of FIG.

6 primarily in that these later embodiments incorporate imaging elements for use in ultrasound imaging techniques.

Looking first at the embodiment shown in FIG. 14, this drive shaft includes at least one ultrasound transducer element 260, and desirably includes a plurality of such elements arranged in diametrically opposed pairs spaced generally circumferentially within the enlarged diameter segment 230. Although these ultrasound transducer elements can be positioned essentially anywhere within the drive shaft, it is believed best to place them with at least a portion of the length of the transducer element 260 positioned generally radially inwardly of a space between adjacent wire turns of the outer helical coil. This will help ensure that the wire of the outer helical coil will not interfere with the ultrasonic waves emitted by the transducers (schematically illustrated as dotted lines extending outwardly from the enlarged diameter segment).

These ultrasonic transducer elements 260 can be held at the desired position within the enlarged diameter segment 230 simply by embedding them in a flexible bushing 270. In the embodiment of FIG. 14, the bushing has a smaller diameter along most of its length than the inner diameter of the outer helical coil 250. Maintaining a space between the bushing and the outer helical coil will help maximize the flexibility of the enlarged diameter segment 230 by minimizing the impact of the bushing on movement of the wire turns of the outer helical coil 250 with respect to one another.

The bushing may be formed of any suitable sonolucent material, i.e., a material which is relatively transparent to ultrasound waves and minimally reflects or attenuates ultrasonic energy. In order to maximize the flexibility of the enlarged diameter segment, the material of the bushing is optimally highly flexible, as well. Material such as silicone, latex and certain other plastics (e.g., polyethylene) are believed to be suitable for such a sonolucent bushing 270.

The proximal segment 222 of the drive shaft shown in FIG. 14 has been modified slightly from the design shown in FIG. 6. In particular, the adjacent wire turns of the outer helical coil 250 in this proximal segment 222 are not bottomed out in the embodiment shown in FIG. 14. Instead, a generally helical gap 256 is defined by adjacent turns of the wire forming the outer helical coil.

Electrical leads 264 attached to the transducer elements can be received within this generally helical gap 256 between adjacent turns of the wire forming the outer helical coil 250. This permits the leads to extend proximally out of the patient's body for connection to an ultrasound imaging machine (not shown). If so desired, a sheath 223 may be provided along some or all of the proximal segment 222 of the drive shaft.

In contrast to the narrower bushing 270 of the embodiment illustrated in FIG. 14, the bushing 270' of the drive shaft 220 shown in FIG. 15 substantially fills the space between the exterior of the inner helical coil 240 and the interior surface of the outer helical coil 250 throughout the entire enlarged diameter segment 230. This larger bushing 270' may be formed of the same materials discussed above for the bushing 270. This bushing may also serve to bond the inner helical coil 240 and outer helical coil 250 in much the same fashion as the bonds 236 in FIG. 14. For purposes of completeness, a distal bond 236 is illustrated in FIG. 15 to indicate that at least one of these bonds could remain. In most instances, though, the bushing 270' will likely obviate the need to include such a bond 236.

The drive shaft 220 shown in FIG. 15 also includes at least one signal processor 262, and preferably includes a plurality of such processors 262, as shown. These processors may be positioned distally of the transducer elements 260' and may be positioned closer to the inner helical coil 240 than are the transducer elements 260'. These processors receive the signals from the transducer elements and relay these signals back to the ultrasound imaging machine (not shown) by means of the leads 264. For purposes of clarity, leads between the transducer elements 260' and the processors 262 are not shown in FIG. 15, but it is to be understood that these transducer elements are connected to the processors. The processors 262 may comprise little more than amplifiers to boost the signal received from the transducer elements 260'. These processors could also perform at least some rudimentary signal processing before delivering the signal to the ultrasound imaging machine through the leads. Such processors are known in the art and are already incorporated into some commercially available ultrasound imaging catheters.

Figure 16:
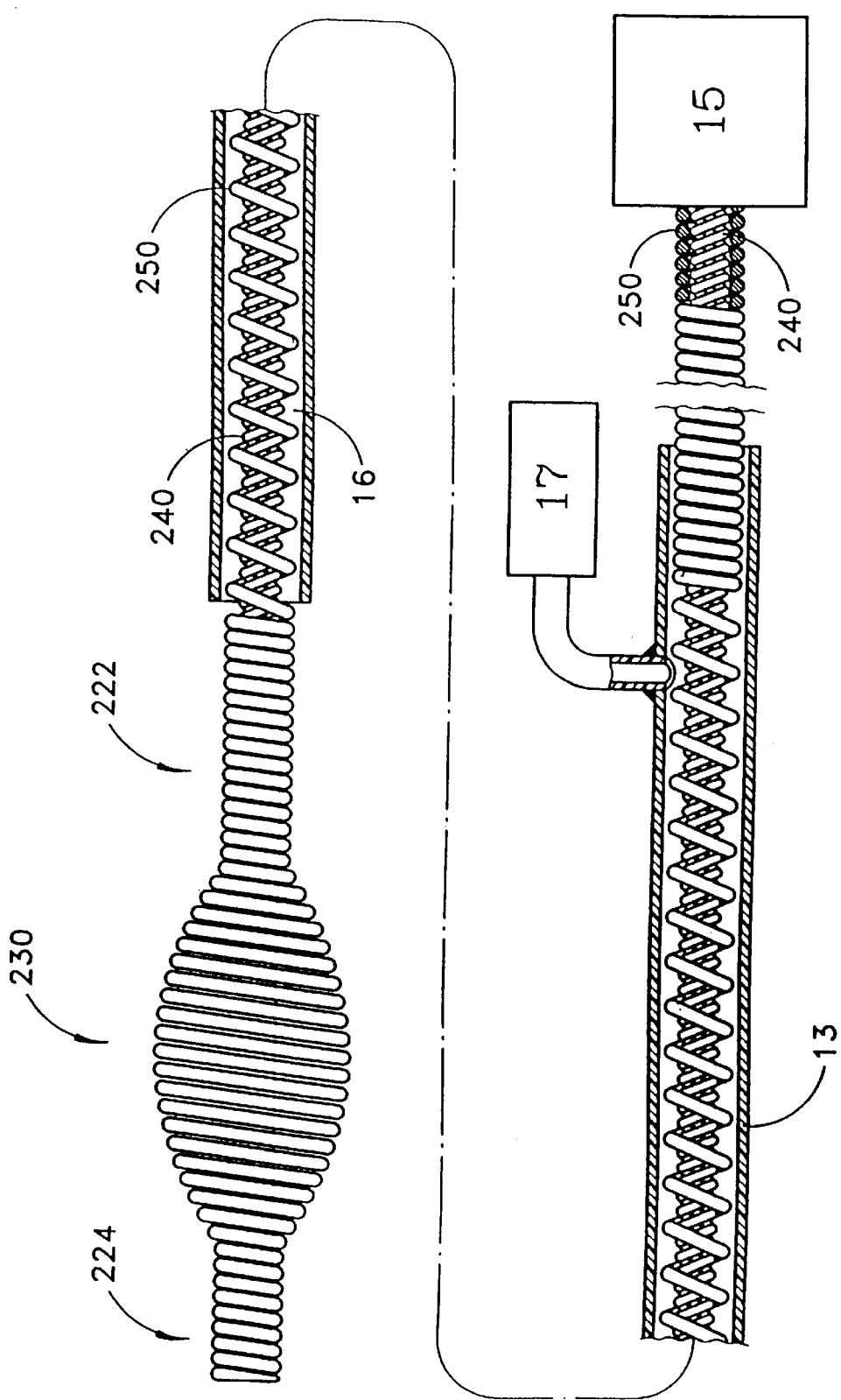
FIG. 16 is a schematic view of a modified embodiment of the invention having spaces between adjacent wire turns along most of the length of the outer layer of the proximal segment of the drive shaft.

FIG. 16 illustrates another embodiment of the invention. This embodiment illustrates a useful modification of the proximal segment 222 of the drive shaft 220 shown in FIG. 6. It is to be understood, though, that the modification of the drive shaft illustrated in FIG. 16 could be used to equal advantage in any of the other embodiments of the invention discussed above.

The drive shaft of FIG. 16 has the same basic structure as the dual-coil drive shafts discussed above. In particular, the drive shaft generally includes an inner helical coil 240 received within a lumen of an outer helical coil 250. These inner and outer wire layers are desirably helically wound in opposite directions so that the outer layer tends to radially contract and the inner layer tends to radially expand when the drive shaft is rotated in a predetermined direction by the driver 15. If so desired, the inner helical coil may be multi-filar while the outer helical coil is a mono-filar coil, but that may not be necessary in connection with the present embodiment.

The primary distinction between the drive shaft shown in FIG. 16 and the general embodiments of a drive shaft discussed above is that the present drive shaft provides a generally helical gap 16 between adjacent turns of the outer helical coil 250 along at least a portion of the proximal segment 222. In a preferred embodiment, this helical gap 16 extends along a majority of the length of the catheter 13 within which the drive shaft is received. When the drive shaft is in use, this gap 16 desirably extends from a position outside the patient's body to a position located distally close to or even beyond the distal end of the catheter 13.

A fluid source 17 is provided in fluid communication with the lumen of the catheter 13 outside the patient's body. The fluid source may provide, for example, a saline solution or a radiographic contrast medium. This fluid flowing within the catheter will serve to both lubricate and cool the system, minimizing any problems due to friction between the drive shaft and the catheter when the drive shaft is rotated at high speeds.

The helical gap 16 in the outer helical coil 250 serves to urge fluid from the fluid source 17 distally along the catheter 13. The lumen of the catheter 13 is desirably somewhat larger than the outer diameter of the outer helical coil 250 when the drive shaft is rotated. Accordingly, there is no clear helical space defined within the catheter to pump fluids. Nonetheless, the rotation of the gap 16 as the drive shaft is rotated will help induce a distal fluid flow within the catheter.

One other point worth noting about FIG. 16 is the illustration of gaps between adjacent turns of the wire or wires of the inner helical coil 240. As noted above in connection with FIG. 2, for example, it is preferred that the inner helical coil be formed so that it is essentially bottomed out along the proximal segment of the drive shaft. As a practical matter, even a "bottomed out" coil formed on a mandrel will tend to have adjacent turns of the wire separated slightly from one another. Although the size of the gaps between adjacent turns of the inner helical coil is exaggerated in FIG. 16, these gaps are substantially smaller than the helical gap 16 in the outer helical coil, permitting the drive shaft to pump fluid relatively effectively.

While a preferred embodiment of the present invention has been described, it should be understood that various changes, adaptations and modifications may be made therein without departing from the spirit of the invention and the scope of the appended claims.

What is claimed is:

1. A method of forming an elongate, flexible drive shaft, the method comprising:
    a. forming an inner helical coil by winding a plurality of wires about a forming mandrel, the resulting inner helical coil having a lumen and a proximal end;
    b. forming an outer helical coil by winding a single wire with a mandrel-less coil forming machine, the resulting outer helical coil having a lumen and a proximal end; and
    c. positioning the inner helical coil within the lumen of the outer helical coil to define a drive shaft, the inner and outer helical coils being oriented such that the inner helical coil is wound in a direction opposite that in which the outer helical coil is wound.

2. The method of claim 1 further comprising the step of attaching the proximal ends of the inner and outer helical coils to a common driver and driving the driver to rotate the drive shaft.

3. The method of claim 1 wherein the inner helical coil is formed from three separate wires, each wire being wound adjacent at least one other wire.

4. The method of claim 1 wherein the wire of the outer helical coil is wound to define a helical gap along at least a proximal segment of the drive shaft.

5. The method of claim 4 further comprising the step of placing the proximal segment of the drive shaft in a lumen of a catheter, the helical gap urging fluid distally within the catheter when the drive shaft is rotated in a predetermined direction.

6. The method of claim 1 wherein the coils are rotated such that the outer and inner helical coils are urged into radially compressive engagement with one another.

7. The method of claim 1 wherein the outer diameter of the outer helical coil is varied along its length.

8. The method of claim 7 wherein the outer diameter of the inner helical coil is maintained substantially constant along its length.

9. The method of claim 1 wherein the drive shaft has proximal, intermediate and distal segments, wherein the diameters of the wire turns of the outer helical coil along the intermediate segment are gradually increased distally through a proximal portion of such intermediate segment and gradually decreased distally through a distal portion of such intermediate segment, thereby defining an enlarged diameter segment of the outer helical coil.

10. The method of claim 9 further comprising spacing adjacent wire turns of the outer helical coil from one another along at least part of the intermediate segment, the spacing between adjacent wire turns being gradually increased distally through said proximal portion of such intermediate segment and gradually decreased distally through said distal portion of such intermediate segment.

11. The method of claim 9 further comprising spacing at least some adjacent wire turns of the inner helical coil from one another along at least part of the intermediate segment.

12. The method of claim 9 further comprising providing a length of the enlarged diameter segment of the outer helical coil with an abrasive external surface to define an abrasive segment of the drive shaft.

13. The method of claim 12 wherein the abrasive external surface is provided by coating an external surface of the outer helical coil with an abrasive material.

14. The method of claim 13 wherein the abrasive material is coated on the outer helical coil by applying a binder to the coil.

15. The method of claim 14 wherein the binder is used to bond adjacent wire turns of the outer helical coil to one another along the abrasive segment.

16. The method of claim 9 wherein the diameters of the wire turns of the outer helical coil along the proximal portion of the intermediate segment are increased distally at a generally constant rate, thereby forming generally the shape of a cone.

17. The method of claim 16 further comprising providing a length of the enlarged diameter segment of the outer helical coil with an abrasive external surface to define an abrasive segment of the drive shaft.

18. The method of claim 17 wherein the abrasive external surface is provided by coating an external surface of the outer helical coil with an abrasive material.

19. The method of claim 9 or claim 18 further comprising bonding at least some of the wire turns of the outer helical coil to one another along the abrasive segment.

20. The method of claim 16 further comprising spacing at least some adjacent wire turns of the inner helical coil from one another along at least part of the intermediate segment.

21. The method of claim 9 further comprising bonding the inner helical coil to the outer helical coil adjacent at least one end of the intermediate segment.

22. The method of claim 21 wherein, along the intermediate segment of the drive shaft, the inner helical coil is permitted to move with respect to the outer helical coil such that when the intermediate segment of the drive shaft is bent around a curve, axes of the inner helical coil and the outer helical coil do not coincide with one another.

23. A method of forming an elongate, flexible rotational atherectomy device, the method comprising:
    a. forming an inner helical coil by winding a plurality of wires about a forming mandrel, the inner helical coil having a lumen, an intermediate segment and a proximal end, at least some adjacent wire turns being spaced from one another along at least part of the intermediate segment;
    b. forming an outer helical coil by winding a single wire with a mandrel-less coil forming machine, the resulting outer helical coil having a lumen, an intermediate segment and a proximal end, the diameters of the wire turns being gradually increased distally through a proximal portion of the intermediate segment and gradually decreased distally through a distal portion of the intermediate segment, thereby defining an enlarged diameter segment of the outer helical coil;
    c. positioning the inner helical coil within the lumen of the outer helical coil to define a drive shaft, the intermediate segment of the inner helical coil being positioned generally within the intermediate segment of the outer helical coil, the inner and outer helical coils being oriented such that the inner helical coil is wound in a direction opposite that in which the outer helical coil is wound; and d. providing a length of the enlarged diameter segment of the outer helical coil with an abrasive external surface to define an abrasive segment of the drive shaft.

24. The method of claim 23 wherein the abrasive external surface is provided by coating an external surface of the outer helical coil with an abrasive material.

25. The method of claim 23 further comprising attaching the proximal ends of the inner and outer helical coils to a common driver and driving the driver to rotate the drive shaft.

26. The method of claim 23 wherein the diameters of the wire turns of the proximal portion of the intermediate segment of the outer helical coil are increased distally at a generally constant rate, thereby forming generally the shape of a cone.

* * * * *